US012800529B2

(12) United States Patent
Torres et al.

(10) Patent No.: US 12,800,529 B2
(45) Date of Patent: Nov. 17, 2026

(54) LIGAND-TARGET INTERACTION ANALYSIS BY PHOTOCHEMICALLY INDUCED DYNAMIC NUCLEAR POLARIZATION (PHOTO-CIDNP) ENHANCED NMR SPECTROSCOPY

(71) Applicant: ETH Zurich, Zurich (CH)

(72) Inventors: Felix Torres, Oberglatt (CH); Roland Pascal Riek, Zurich (CH); Matthias Butikofer, Zurich (CH)

(73) Assignee: ETH Zurich, Zurich (CH)

( * ) Notice: Subject to any disclaimer, the term of this patent is extended or adjusted under 35 U.S.C. 154(b) by 470 days.

(21) Appl. No.: 18/294,558

(22) PCT Filed: Aug. 3, 2022

(86) PCT No.: PCT/EP2022/071777
§ 371 (c)(1),
(2) Date: Feb. 2, 2024

(87) PCT Pub. No.: WO2023/012203
PCT Pub. Date: Feb. 9, 2023

(65) Prior Publication Data

US 2024/0345008 A1 Oct. 17, 2024

(30) Foreign Application Priority Data

Aug. 3, 2021 (EP) .................................... 21189289

(51) Int. Cl.
*G01N 1/14* (2006.01)
*G01N 24/08* (2006.01)
*G01N 33/50* (2006.01)

(52) U.S. Cl.
CPC ............. *G01N 24/088* (2013.01); *G01N 1/14* (2013.01); *G01N 33/5008* (2013.01)

(58) Field of Classification Search
CPC ..... G01N 24/088; G01N 1/14; G01N 33/5008
(Continued)

(56) References Cited

U.S. PATENT DOCUMENTS 7,501,236 B1 * 3/2009 Knox .................. G01R 33/281
435/6.11
2004/0082075 A1 4/2004 Powers
(Continued)

FOREIGN PATENT DOCUMENTS

EP 2407796 A1 1/2012

OTHER PUBLICATIONS

Lawler, R. G. et al, Review of Scientific Instruments 1974, 45, 84-86. (Year: 1974).*
(Continued)

*Primary Examiner* — Arlen Soderquist
(74) *Attorney, Agent, or Firm* — Renner, Otto, Boisselle & Sklar, LLP

(57) ABSTRACT

A method for detecting and/or characterizing a ligand-target binding based on photochemically induced dynamic nuclear polarization (photo-CIDNP) enhanced NMR spectroscopy, comprising the steps: (a) irradiating a sample (A) comprising a photosensitizer and a ligand to excite the photosensitizer and induce dynamic nuclear polarization of the ligand by the photosensitizer, (b) recording an NMR spectrum of sample (A), repeating steps (a) and (b) with a sample comprising sample (A) and further comprising a target of interest, and (c) comparing the NMR spectra of samples (A) and (B) and detecting and/or characterizing a ligand-target binding based on at least one difference in the NMR spectra. The present invention further pertains to a device for conducting the method.

27 Claims, 10 Drawing Sheets

Figure 1:
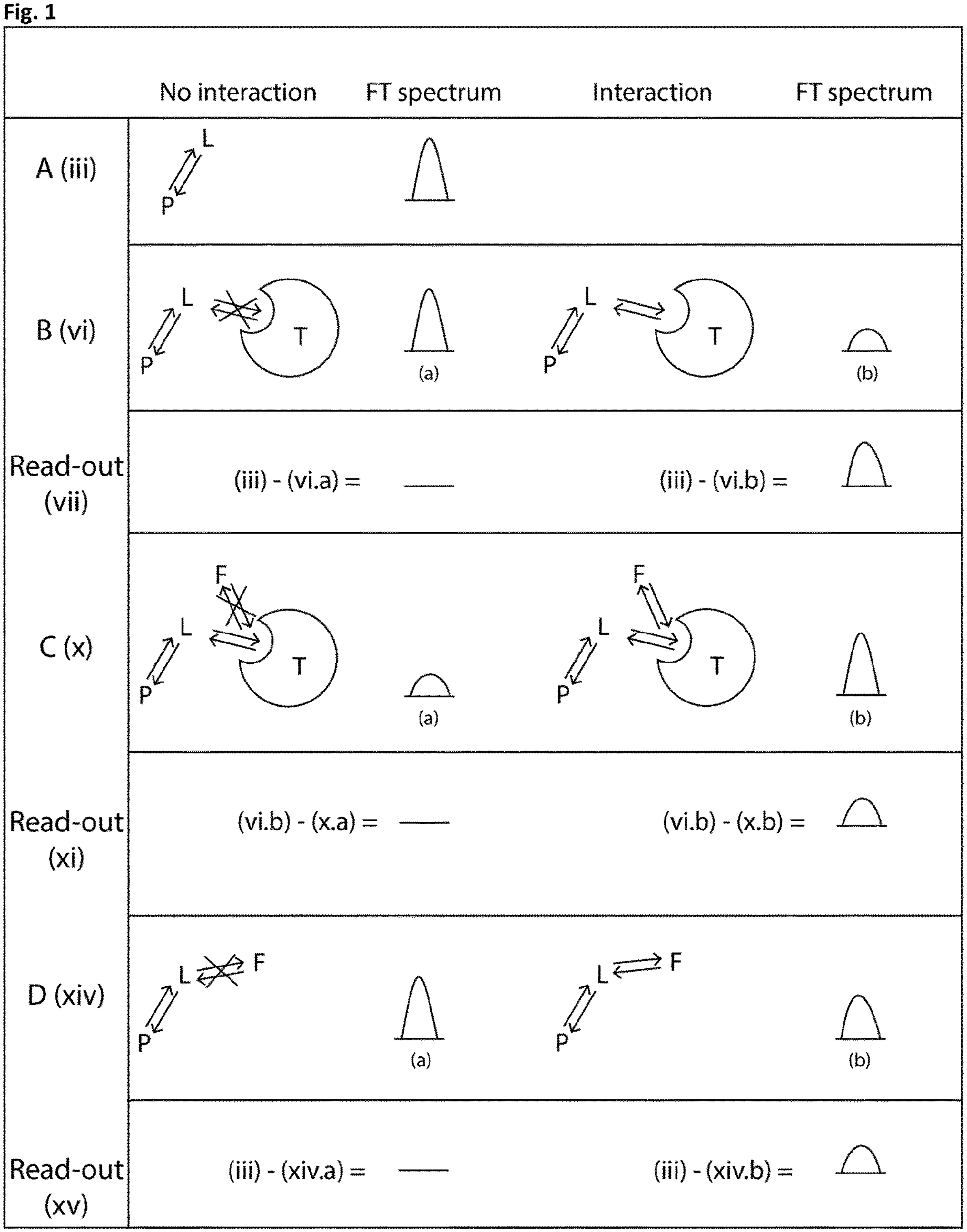

Specification includes a Sequence Listing.

(58) Field of Classification Search
USPC .......................................................... 436/173
See application file for complete search history.

(56) References Cited

U.S. PATENT DOCUMENTS

| | | | | |
|---|---|---|---|---|
| 2006/0171891 | A1 | 8/2006 | Ardenkjaer-Larsen et al. | |
| 2014/0117988 | A1* | 5/2014 | Annino ............. | G01R 33/3456 324/309 |
| 2020/0072932 | A1* | 3/2020 | Van Zijl ............. | G01R 33/5605 |

OTHER PUBLICATIONS

Feeney, J. et al, Biochemistry 1980, 19, 2466-2472. (Year: 1980).*
De Marco, A. et al, Jornal of Biological Chemistry 1986, 261, 13510-13516. (Year: 1986).*
Marko, J. et al, Photochemistry and Photobiology 1988, 47, 1-13. (Year: 1988).*
De Marco, A. et al, Biochimica et Biophysica Acta 1989, 994, 121-137. (Year: 1989).*
Siebert, H.-C. et al, Proteins: Structure, Function, and Genetics 1997, 28, 268-284. (Year: 1997).*
Chen, A. et al, Journal of the American Chemical Society 1998, 120, 10258-10259. (Year: 1998).*
Chen, A. et al, Journal of the American Chemical Society 2000, 122, 414-415. (Year: 2000).*
Dalvit, C. et al, Journal of the American Chemical Society 2002, 124, 7702-7709. (Year: 2002).*
Siebert, H.-C. et al, Biochemistry 2002, 41, 9707-9717. (Year: 2002).*
Mok, K. H. et al, Journal of the American Chemical Society 2003, 125, 12484-12492 (Year: 2003).*
Wang, Y.- S. et al, Magnetic Resonance in Chemistry 2004, 42, 485-489. (Year: 2004).*
Polyakov, N. E. et al, Photochemistry and Photobiology 2004, 80, 565-571. (Year: 2004).*
Siebert, H.-C. et al, in NMR Spectroscopy and Computer Modeling of Carbohydrates 2006, ACS Symposium Series, Vliegenthar and Woods (eds), American Chemical Society: Washington, DC, 81-113. (Year: 2006).*
Assadi-Porter, F. M. et al, Journal of the American Chemical Society 2008, 130, 7212-7213 with 3 pages of supplemental information. (Year: 2008).*
Viegas, A. et al, Journal of Chemical Education 2011, 88, 990-994 with 36 pages of supplementary material. (Year: 2011).*
Angulo, J. et al, European Biophysics Journal 2011, 40, 1357-1369. (Year: 2011).*
Lukzen, N. et al, Applied Magnetic Resonance 2011, 41, 325-336. (Year: 2011).*
Lee, J. H. et al, Journal of Physical Chemistry B 2013, 117, 6069-6081 with 15 pages of supporting text. (Year: 2013).*
Harner, M. J. et al, Journal of Biomolecular NMR 2013, 56, 65-75. (Year: 2013).*
Unione, L. et al, Medicinal Chemistry Communications 2014, 5, 1280-1289. (Year: 2014).*
Mondal, M. et al, Chemical Society Reviews 2015, 44, 2455-2488. (Year: 2015).*
Aguirre, C. et al, Current Protocols in Protein Science 2015, 81, 17.18.1-17.18.24. (Year: 2015).*
Min, H. et al, ChemMedChem 2015, 10, 1559 - 1563. (Year: 2015).*
Plainchont, B. et al, Analytical Chemistry 2018, 90, 3639-3650. (Year: 2018).*
F. Buck, et al.: “Photochemically induced dynamic nuclear polarization investigation of complex formation of the NH2-terminal DNA-binding domain of lac repressor with poly[d(AT)]”, Proc. Natl. Acad. Sci. USA, vol. 77, No. 9, Sep. 1980 (Sep. 1980), pp. 5145-5148, XP009532592, p. 5145, col. 2, paragraph 2.
Philipp Nitschke, et al.: “Combination of illumination and high resolution NMR spectroscopy: Key features and practical aspects, photochemical applications, and new concepts”, Progress in Nuclear Magnetic Resonance Spectroscopy, Pergamon Press, Oxford, GB, vol. 114, Jun. 5, 2019 (Jun. 5, 2019), pp. 86-134, XP085921087, ISSN: 0079-6565, DOI: 10.1016/J.PNMRS.2019.06.001 [retrieved on Jun. 5, 2019] sections 2.2.2, 3 and 1.
Alvar D. Gossert, et al.: “NMR in drug discovery: A practical guide to identification and validation of ligands interacting with biological macromolecules”, Progress in Nuclear Magnetic Resonance Spectroscopy, vol. 97, Sep. 30, 2016 (Sep. 30, 2016), pp. 82-125, XP029819915, ISSN: 0079-6565, DOI: 10.1016/J.NMRS.2016.09.001 chapter 2.
Kim Yaewon, et al.: “Applications of Dissolution-DNP for NMR Screening” In: Biomembranes Part R: Transport theory: cells and model membranes; In: Methods in Enzymology11, 2019, Academic Press, XP055877434, ISSN: 0076-6879 ISBN: 978-0-12-182072-5 vol. 615, pp. 501-526, DOI: 10.1016/bs.mie.2018.08.016, p. 5-p. 9.
Felix Torres, et al.: “Molecular features toward high photo-CIDNP hyperpolariztion explored through the oxidocyclization of tryptophan”, Physical Chemistry Chemical Physics, vol. 23, No. 11, Mar. 25, 2021 (Mar. 25, 2021), pp. 6641-6650, XP055877416, ISSN: 1463-9076, DOI: 10.1039/DOCP06068B p. 6649, right-hand column, paragraph 1.
Kaptein et al., Laser photo-CIDNP as a surface probe for proteins in solution, 1978, Nature vol. 274, p. 293-294, https://doi.org/10.1038/274293a0, Only an abstract submitted.
Serikawa et al., Determination of the DNA binding site of the GAL4 protein, 1992, FEBS vol. 299, p. 205-208.
Okuno, et al., Fluorescein: A photo-CIDNP sensitizer enabling hypersensitive NMR data collection in liquids at low micromolar concentration, J Phys Chem B, vol. 120, p. 715-723.
A. Sobol, et al., Atto Thio 12 as a promising dye for photo-CIDNP, J. Chem. Phys. 151, 234201 (2019), https://doi.org/10.1063/1.5128575, Only an abstract submitted.
Wang, An exact mathematical expression for describing competitive binding of two different ligands to a protein molecule, FEBS letter, 1995, vol. 360, p. 111-114.

* cited by examiner

Figure 2:
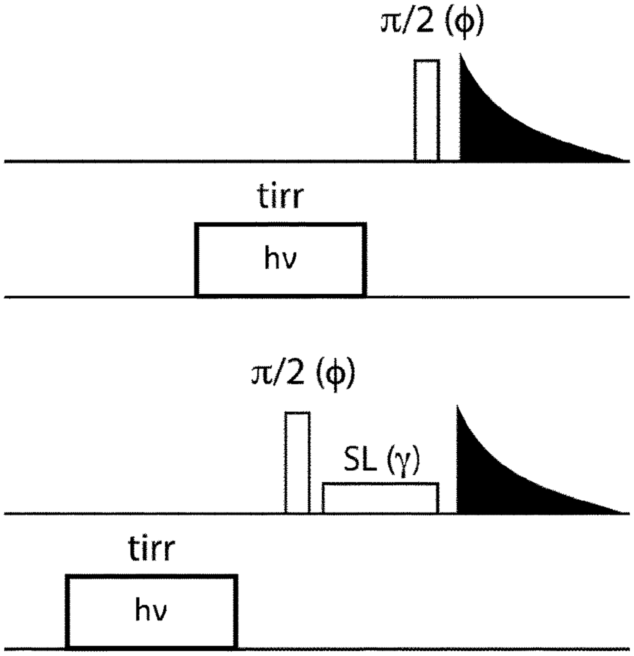
Figure 2:
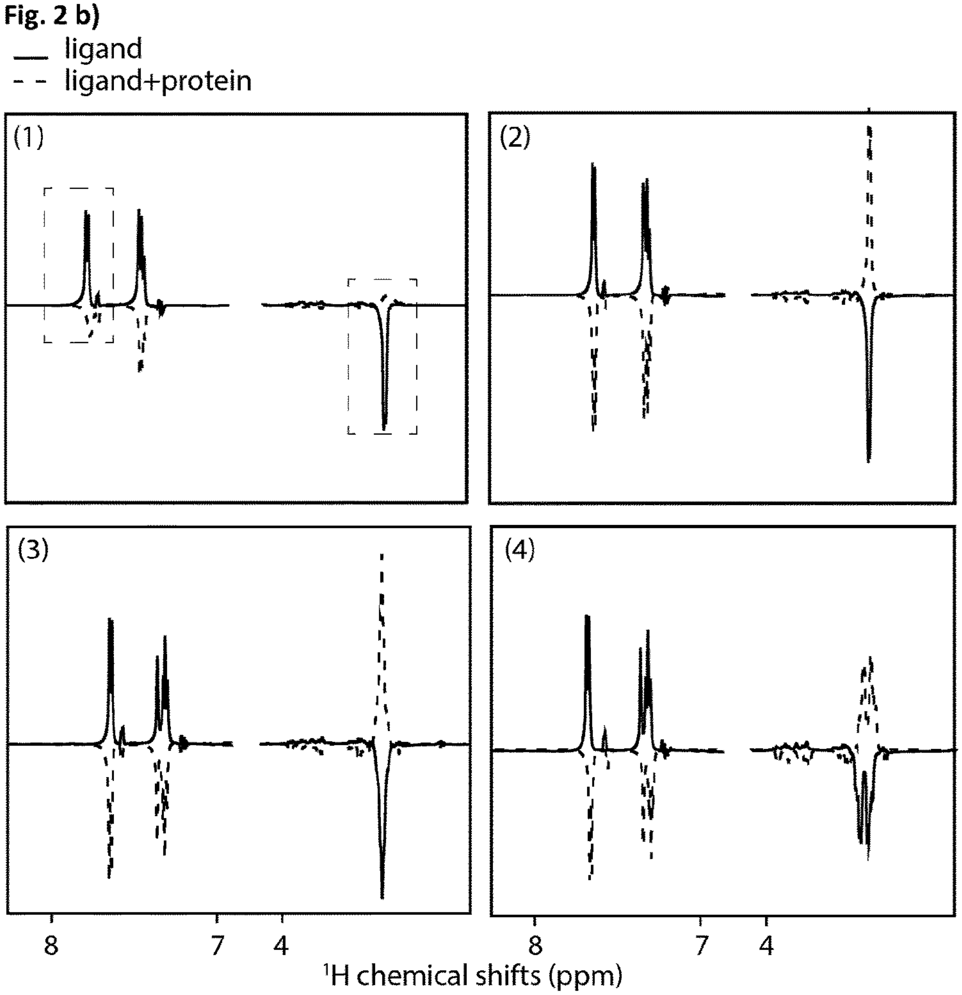
Figure 2:
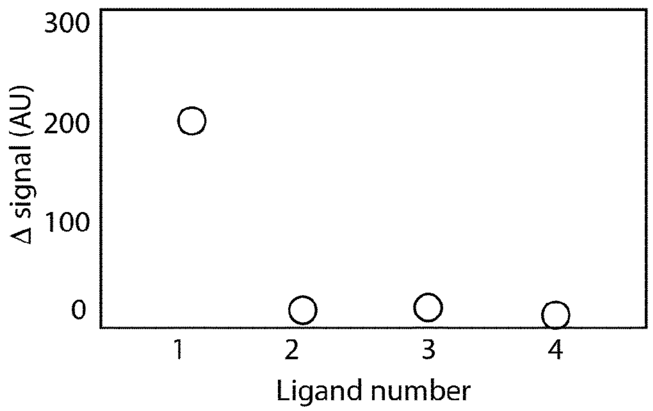
Figure 2:
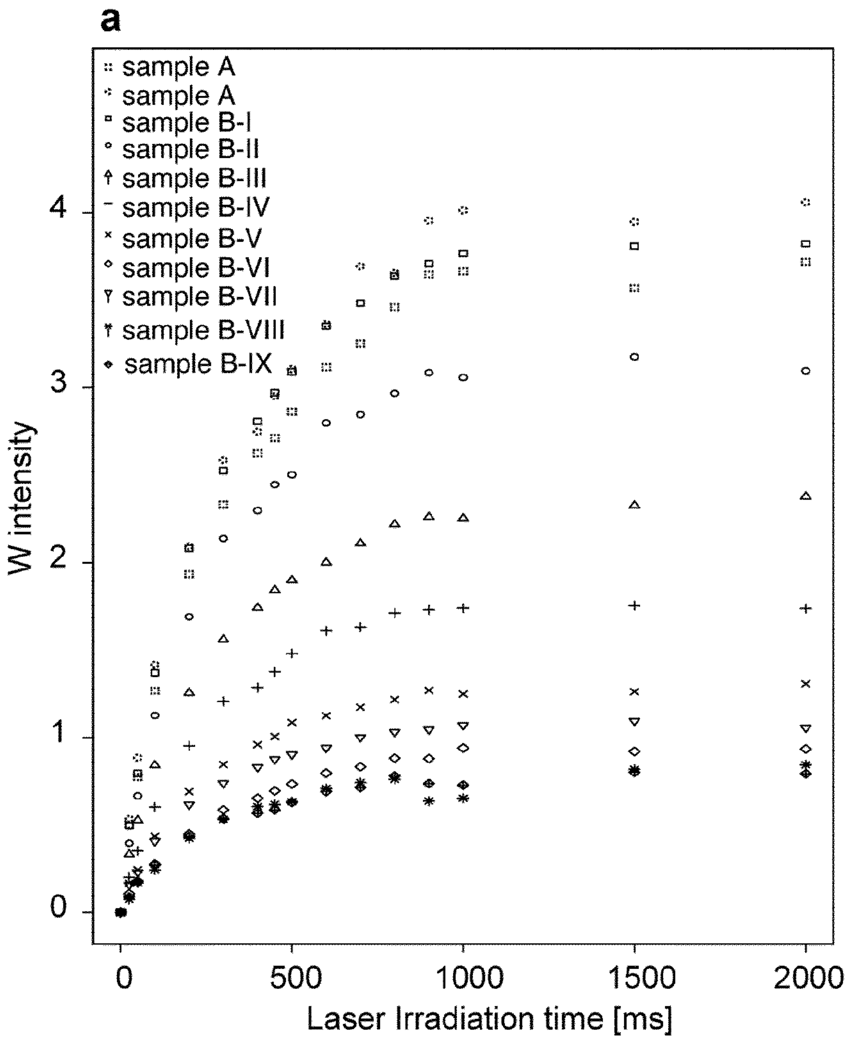

Fig. 2 d) (cont.)
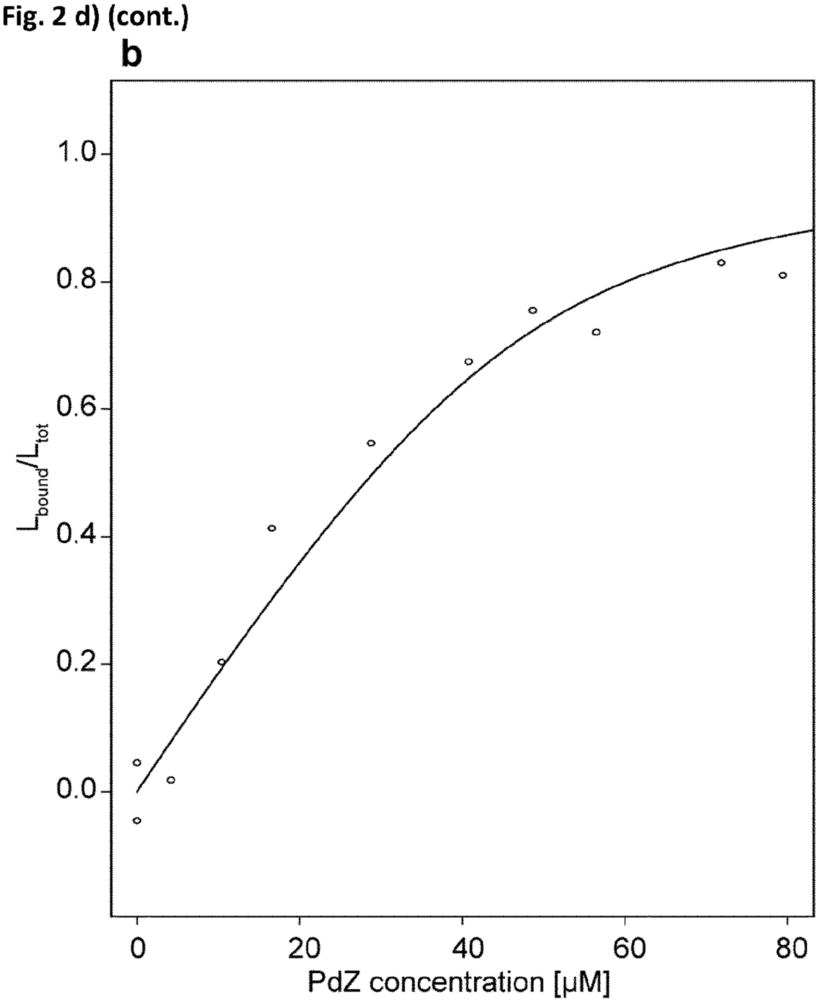

LIGAND-TARGET INTERACTION ANALYSIS BY PHOTOCHEMICALLY INDUCED DYNAMIC NUCLEAR POLARIZATION (PHOTO-CIDNP) ENHANCED NMR SPECTROSCOPY

This application is a national phase of International Patent Application No. PCT/EP2022/071777 filed Aug. 3, 2022, which claims priority to European Patent Application No. 21189289.8 filed Aug. 3, 2021, each of which is hereby incorporated herein by reference in its entirety.

The present invention pertains to a method for detecting and/or characterizing a ligand-target binding based on photochemically induced dynamic nuclear polarization (photo-CIDNP) enhanced NMR spectroscopy, comprising the steps: (a) irradiating a sample (A) comprising a photosensitizer and a ligand to excite the photosensitizer and induce dynamic nuclear polarization of the ligand by the photosensitizer, (b) recording an NMR spectrum of sample (A), repeating steps (a) and (b) with a sample (B) comprising sample (A) and further comprising a target of interest, and (c) comparing the NMR spectra of samples (A) and (B) and detecting and/or characterizing a ligand-target binding based on at least one difference in the NMR spectra. The present invention further pertains to a device for conducting the method.

BACKGROUND

Present methods for assessing and analyzing ligand-target interactions, e.g., in biophysics, are based on X-ray crystallography, surface plasmon resonance (SPR), and fluorescence assays. However, all of these methods suffer specific problems inherent to their biophysics: 1) X-ray crystallography requires crystals which are laborious and slow to obtain and cannot be formed by all ligands or targets. 2) X-ray crystallography does not provide information on the affinity (constant) of the ligand for its target. 3) X-ray crystallography screening is performed by soaking which requires high ligand concentrations (5-20 mM). 4) SPR requires the immobilization of the target onto a surface. 5) The target-ligand complex structure cannot be analyzed or determined with SPR. 6) SPR and X-ray crystallography both suffer from false positives and cross-confirmation is tedious. 7) Fluorescence assays are not versatile, for each target a specific solution is designed. And 8) Fluorescence assays have very high false-positive rates.

Nuclear magnetic resonance (NMR) spectroscopy can be used for assessing and analyzing ligand-target interactions, and the analysis can be assisted by heteronuclear single quantum coherence (HSQC) spectroscopy and saturation transfer diffusion (STD). Moreover, nuclear Overhauser effect spectroscopy (NOESY) provides data to calculate molecular structures in solution. However, NMR spectroscopy also suffers from intrinsic limitations: 1) STD and HSQC take a lot of time to perform: 30 min-1 hour/molecule. 2) STD requires a high concentration of ligand (2 to 0.1 mM), increasing the costs and the risk of false positives. 3) STD NMR does not detect binders in the slow exchange regime, i.e., strong binders. 4) HSQC spectroscopy requires a 15N-labeled target at a relatively high concentration (1.0-0.05 mM). 5) NOESY experiments are time consuming (24 to 48 hours). 6) NOESY experiments require filtering the signal of the target. This decreases the sensitivity and requires double labeling the target (with $^{13}C$ and $^{15}N$) increasing the price of target production considerably. 7) Sensitive NMR requires expensive high field magnets.

Photo-CIDNP enhanced NMR spectroscopy has been used to distinguish between exposed and buried amino acids in a protein (Kaptein et al. 1978, Nature Vol. 274, p. 293-294). Other studies based on Kaptein et al. have used photo-CIDNP enhanced NMR spectroscopy to explore the signals of exposed amino acids in proteins when a potential target binds (Serikawa et al. 1992, FEBS Vol. 299, p. 205-208). These studies share the drawback that exposed residues of the target need to be identified, and that the NMR-signals of the target need to be assigned before analysis which is limiting the type of binding that can be observed, is time consuming and difficult to achieve for complex targets. Moreover, these studies are only possible if a photo-CIDNP sensitive residue (i.e., tyrosine, tryptophan, histidine) is located in the binding site.

It is the objective technical problem of the present invention to provide a method for the improved detection and/or characterization of a ligand-target binding.

In a first aspect, the present invention is directed to a method for detecting and/or characterizing a ligand-target binding based on photochemically induced dynamic nuclear polarization (photo-CIDNP) enhanced NMR spectroscopy, the method comprising the following steps:

(i) providing a sample (A) comprising a photosensitizer and a ligand, wherein the photosensitizer is suitable for chemically inducing dynamic nuclear polarization of the ligand upon irradiation of the sample;
(ii) irradiating sample (A) at a wavelength and duration suitable for exciting the photosensitizer and under conditions allowing for chemically induced dynamic nuclear polarization of the ligand by the photosensitizer;
(iii) recording an NMR spectrum of sample (A);
(iv) providing a sample (B) comprising sample (A) and further comprising a target of interest;
(v) irradiating sample (B) under the conditions of step (ii);
(vi) recording an NMR spectrum of sample (B); and
(vii) comparing the NMR spectra of steps (iii) and (vi) and detecting and/or characterizing a ligand-target binding based on at least one difference in the NMR spectra of steps (iii) and (vi).

It was surprisingly found that inducing dynamic nuclear polarization in a ligand before and during binding to a target, as well as comparing the NMR-spectra of these two states, provides an efficient, fast and robust tool for detecting and/or characterizing a ligand-target interaction. The signal enhancement for NMR spectroscopy by photo-CIDNP is in the order of 5-500 times and the present method essentially only requires detection of ligand (and not necessarily target) signals, which allows for the use of low ligand and target concentrations, the detection of fast and slow ligand-target interactions, and a high frequency of measurements with different ligands and/or targets within the same experimental setup which can be used in high throughput screenings. Also, no labelling of the target (or the ligand) is required and the NMR signals do not need to be assigned to the chemical entities of the target (or the ligand). The high polarization of the ligand also allows for the use of economical low field benchtop NMR spectrometers (e.g., 0.9 to 2.3 Tesla).

The term detecting and/or characterizing, as used herein, refers to the detection of a binding of a ligand to a target (identification of a binding ligand), the rate of the association/dissociation of the ligand to the target, as well as the characterization of the ligand-target-complex structure. The binding includes any type of binding, direct binding to an active site as well as allosteric binding.

The term photochemically induced dynamic nuclear polarization (photo-CIDNP) is understood as commonly used in the art. The terms “photochemically induced dynamic polarization” and “chemically induced dynamic polarization” are used herein interchangeably in view of the photochemical excitation of the photosensitizer followed by the chemical interaction of the photosensitizer with the ligand to induce said polarization.

The ligand for use in the present method can be any ligand that is susceptible to photochemically induced dynamic nuclear polarization. The skilled person can determine whether a ligand is susceptible to photo-CIDNP based on its chemical structure and, e.g., in routine experiments detailed below (see, e.g., Example 1).

Suitable photosensitizers are known in the art (see, e.g., Sobol et al., J Chem Phys, Vol 151, art num 234201; Okuno et al., J Phys Chem B, Vol 120, p 715-723) The skilled person can routinely choose a suitable photosensitizer and verify its suitability in Example 1.

Unless specifically stated otherwise, all method steps disclosed herein, in particular method steps involving irradiation and/or NMR recording, e.g. steps (ii) and (iii) for sample (A) and/or (v) and (vi) for sample (B), may be repeated as often as deemed necessary or beneficial, e.g. to increase the signal to noise ratio.

The step of irradiation in all aspects and embodiments disclosed herein is performed at a wavelength which excites the photosensitizer. These wavelengths are either known for the photosensitizers or can be determined by standard assays, such as absorption measurements. Suitable wavelengths for photosensitizers in the context of photo-CIDNP in all aspects and embodiments disclosed herein include, e.g., 408, 450, 520, 532 and 638 nm.

The duration of irradiation can be routinely determined by the skilled person, e.g., by verifying the enhancement ratio build-up curve with time. Exemplary and non-limiting irradiation durations include, e.g., 0.01 to 1 s, or 1 to 4 s.

The sample for use in the present method can be in any form that is suitable for chemically inducing dynamic nuclear polarization, for enabling ligand-target binding and for recording NMR spectra. These forms include complete solution of the components of the sample or partial solution of the components. For example, the target can be suspended or immobilized. Suitable solvents for NMR spectroscopy are known in the art and include, e.g., water, deuterated water, DMSO, acetonitrile, and/or DMF.

Any NMR-active nucleus can be chosen for recording the NMR spectrum.

In an embodiment, the method of the present invention is one, wherein the NMR spectrum is selected from the group consisting of a $^{1}H$, $^{13}C$, $^{15}N$, $^{19}F$ and $^{31}P$ spectrum.

Typically, a one-dimensional NMR spectrum, e.g., a $^{1}H$-NMR spectrum, is sufficient for conducting the method according to the present invention. However, 2D spectra can be used as detailed further below.

The step of providing a sample (B) comprising sample (A) and further comprising a target of interest, and any other step involving a ligand-target binding sample, includes that the step is conducted such that a ligand to target binding is possible, e.g., by providing sufficient time for a potential interaction and by conducting the step under conditions (e.g., at temperatures) which would enable a potential ligand-target interaction.

The step of comparing the NMR spectra of steps (iii) and (vi) and detecting and/or characterizing a ligand-target binding based on at least one difference in the NMR spectra of steps (iii) and (vi) means that this step reveals whether the ligand and target used in the method actually bind to each other. The at least one difference may be in the free induction decay (FID) signal or in the Fourier-transformed (FT) spectrum as detailed further below.

“A difference in the NMR spectra” means that the two NMR spectra differ in at least one signal resulting from the observed nuclei, which signal and difference is above the noise level of the recorded spectrum. The difference can be observed optionally by comparing the signal peak intensity or the peak integral of the same signal(s) in at least two spectra. The level of expected signal difference for different ligand affinities can be calculated from the equations (3) to (8) detailed below. The signal for which a difference is observed is any signal which is observed in the spectrum of sample (A), e.g., a signal characteristic of the ligand.

In the following, an exemplary, non-limiting method according to the present invention is described. A target of interest, e.g., a protein, and a potential ligand for this target, e.g., a (poly-)peptide or a small organic molecule, are selected. Sample (A) is prepared by mixing the potential ligand with a photosensitizer that is suitable for chemically inducing dynamic nuclear polarization of the potential ligand upon irradiation of the sample.

Sample (A) is irradiated for a given time tirr at a given wavelength λ in an NMR spectrometer so that chemically induced dynamic nuclear polarization occurs in the ligand. Subsequently, a radio frequency pulse (e.g., 90°) is emitted for detection and the FID is recorded. Optionally, a spin lock, e.g., up to 105 kHz for about 10 to 200 ms, can be added after the radio pulse. The phase of the optional spin lock is orthogonal to the phase of the detection radio frequency pulse. The optional spin lock typically improves sensitivity, e.g., for weak or slow binding ligands.

For sample (B), the same steps are repeated as outlined for sample (A). Optionally, the phase of the radio pulse (e.g., 90° pulse), and optionally the phase of the spin lock for sample (B) can differ by 180° compared to sample (A).

The NMR spectra of sample (A) and (B), the FID or the FT-FID, are then compared. The presence of at least one difference in the NMR spectra of samples (A) and (B) then indicates a ligand-target binding. If the NMR spectra of samples (A) and (B) were recorded at different radio frequency pulse phases (e.g., 90° and) 180°, the spectra can be added and a sum of zero will indicate the absence of ligand-target binding, while a non-zero sum (i.e., the absolute value of the sum is greater than zero) will indicate the presence of a ligand-target binding. The addition of the spectra is by no means required for this method because the presence of at least one difference in the spectra, e.g., when recorded at the same radio frequency pulse phase for sample (A) and (B), is sufficient for determining the presence of ligand-target binding. However, for simplicity and easier graphic representation, some of the figures disclosed herein result from the addition of the spectra as described herein.

The present method is also suitable for detecting and/or characterizing a further ligand-target binding, wherein the further ligand is essentially not suitable for chemically induced dynamic nuclear polarization. Essentially not suitable for chemically induced dynamic nuclear polarization means that the polarization cannot be induced at all (e.g., as verified in Example 1) or to an extent which is not detectable when comparing the spectra of a further ligand without and with a target.

In an embodiment, the method of the present invention is one, wherein after positively detecting the binding of the ligand to the target in sample (B), the method further comprises the steps:

(viii) providing a sample (C) comprising sample (B) and a further ligand;

(ix) irradiating sample (C) under the conditions of step (ii), wherein the further ligand is essentially not suitable for chemically induced dynamic nuclear polarization and/or wherein the photosensitizer is essentially not suitable for chemically inducing dynamic nuclear polarization of the further ligand;

(x) recording an NMR spectrum of sample (C); and (xi) comparing the NMR spectra of steps (vi) and (x) and detecting and/or characterizing a competitive binding of the further ligand to the target based on at least one difference in the NMR spectra of steps (vi) and (x).

If a competitive binding of the further ligand is detected in the method described herein, the results can optionally be further corroborated as follows.

The term "positively detecting the (competitive) binding of the (further) ligand to the target", as used herein, means that the (further) ligand actually binds to the target.

In an embodiment, the method according to the present invention is one, wherein after positively detecting the competitive binding of the further ligand to the target in sample (C), the method further comprises the steps:

(xii) providing a sample (D) comprising sample (A) and the further ligand of sample (C);

(xiii) irradiating sample (D) under the conditions of step (ii), wherein the further ligand is essentially not suitable for chemically induced dynamic nuclear polarization and/or wherein the photosensitizer is essentially not suitable for chemically inducing dynamic nuclear polarization of the further ligand;

(xiv) recording an NMR spectrum of sample (D); and (xv) comparing the NMR spectra of steps (iii) and (xiv) and validating the detection and/or characterization of the competitive binding of the further ligand to the target based on an absence of a difference in the NMR spectra of steps (iii) and (xiv).

The sample (D) of method step (xii) comprises the further ligand of sample (C) but not the target.

If the comparison of the NMR spectra of steps (iii) and (xiv) do not show a difference, the detection and/or characterization of the competitive binding of the further ligand to the target is confirmed. This can be done, e.g., to further limit the possibility for false-positive results.

The absence of a difference in the NMR spectra, as used herein may be in the free induction decay (FID) signal or in the Fourier-transformed (FT) spectrum. The same definitions apply as provided in the context of the presence of a difference. Generally, the absence of a difference means that the signals in the two spectra do not differ significantly, i.e., that there is essentially no difference in the signals above the noise level of the recorded spectrum. Alternatively, the absence of difference can be defined as the absence of significant difference, where the significance is defined as a difference threshold based on the expected minimum ligand affinities, and can be calculated according the equations (3) to (8) detailed below.

In an embodiment, the method according to the present invention is one, wherein (a) the ligand and/or further ligand is an organic ligand, optionally an organic ligand of about or less than 2 kDa;

(b) the target is an inorganic or organic target, optionally a target of about or more than 2 kDa;

(c) the molecular mass of the ligand and/or further ligand is lower than the molecular mass of the target; and/or (d) the molar ratio between the ligand and/or further ligand and the target is about 1:1 or greater than 1:1 (ligand to target).

Suitable concentrations for the ligand or the further ligand in the sample for use in all aspects and embodiments described herein are, e.g., 0.001 to 5 mM, optionally 0.05 to 0.5 mM.

Suitable concentrations for the target in the sample for use in all aspects and embodiments described herein are, e.g., 0.001 to 1 mM, optionally 0.01 to 0.5 mM.

Suitable concentrations for the photosensitizer in the sample for use in all aspects and embodiments described herein are, e.g., 0.05 to 500 μM, optionally 1 to 100 μM.

Suitable ratios between the photosensitizer and the ligand in the sample for use in all aspects and embodiments described herein are any ration between the ligand and the photosensitizer, e.g., an excess of the ligand to the photosensitizer or an excess of the photosensitizer to the ligand.

In an embodiment, the method according to the present invention is one, wherein the ligand and/or the further ligand are in solution, and/or the target is a solid, an immobilized target or a target in solution.

The ligand, the further ligand, the target and/or the photosensitizer, and further optional components, in a sample for use in all aspects and embodiments described herein are prepared into a sample in a state that allows for NMR spectroscopy, potential ligand-target binding, and photo-CDNP of the ligand. Any combination of complete or partial dissolution of the components, as well as a solid or immobilized state of the components is encompassed by the method of the present invention as long as the method can be conducted.

In an embodiment, the method according to the present invention is one, wherein the ligand comprises a chemical entity selected from the group consisting of (a) monocyclic aromatic $C_5$-$C_7$ and/or a bicyclic aromatic $C_7$-$C_{12}$ moieties substituted by one or more heteroatoms, optionally a heteroatom selected from N, O, S, Se, P, and/or B;

(b) heteromonocyclic aromatic $C_1$-$C_6$ moieties comprising 1 to 5 heteroatoms and/or heterobicyclic aromatic $C_2$-$C_{11}$ moieties comprising 1 to 8 heteroatoms, optionally a heteroatom selected from N, O, S, Se, P, and B; and (c) a secondary or tertiary amine, a sulfoxide, a dialkylsufide, a sulfamide, and a sulfamate.

As used herein, the chemical entity which the ligand comprises is a chemical entity that is suitable for photochemically induced dynamic nuclear polarization with a photosensitizer, e.g., by a radical mechanism, e.g., by electron transfer or proton coupled electron transfer.

The term "monocyclic aromatic $C_5$-$C_7$ moieties" shall be understood to mean a substituted or non-substituted aromatic hydrocarbon cycle containing the number of carbon items indicated, e.g., "monocyclic aromatic ($C_{5-7}$) moieties" from 5 to 7 carbon atoms.

The term "bicyclic aromatic $C_7$-$C_{12}$ moieties" refers to a substituted or non-substituted aromatic hydrocarbon bicycle containing the number of carbon items indicated, e.g., "bicyclic aromatic $C_7$-$C_{12}$ moieties" from 5 to 7 carbon atoms.

The term "heteromono- or heterobicyclic aromatic moieties" refers to a stable substituted or non-substituted, aromatic mono- or bicyclic heteroatom-containing hydrocarbon cycle. Each heterocycle consists of carbon atoms and one or more heteroatoms optionally chosen from N, O, S, Se, P, and B. A heterocycle may contain the number of carbon atoms in addition to the non-carbon atoms as indicated: a "heteromonocyclic aromatic $C_1$-$C_6$ moieties" is meant to have 1 to 6 carbon atoms in addition to a given number of heteroatoms such that an aromatic heterocycle is obtained.

The term "heterobicyclic aromatic moiety" refers to a heterocycle as defined above comprising more than 1 ring, optionally two rings.

Optionally, the mono- or bicyclic aromatic moiety is selected from the group consisting of:

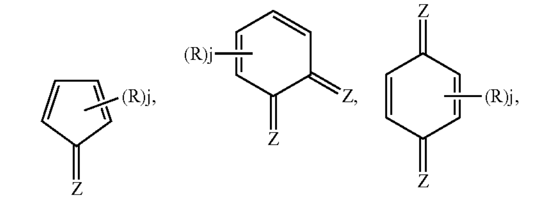
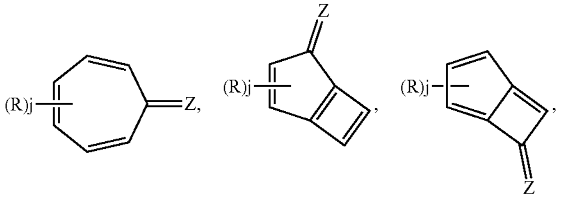
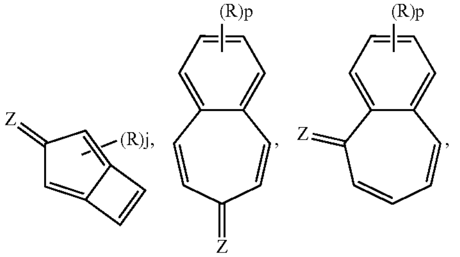
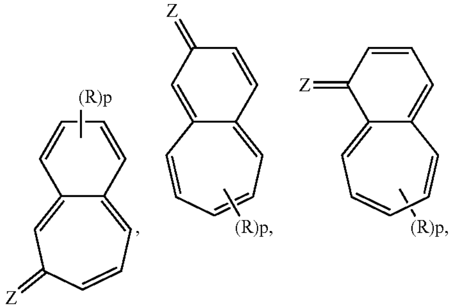
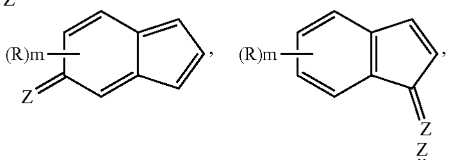
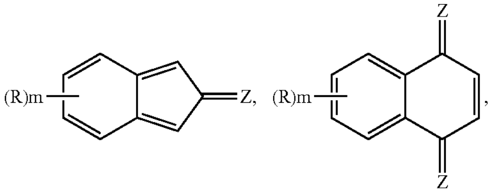
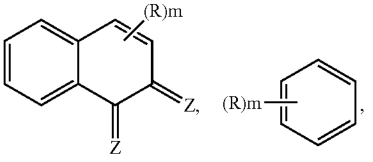

-continued

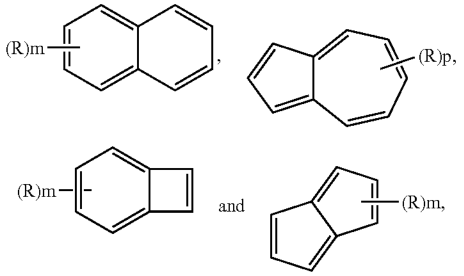

wherein R is independently selected from the group consisting of

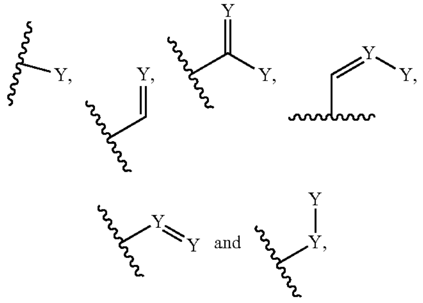

wherein Z and Y are independently selected from the group consisting of N, O, S, Se, P, and B, wherein j is selected from 1 to 4, n is selected from 1 to 5, m is selected from 1 to 6, p is selected from 1 to 8 and wherein the moiety is optionally attached to the ligand at any of the carbon atoms.

Optionally, the heteromono- or heterobicyclic aromatic moiety is selected from the group consisting of:

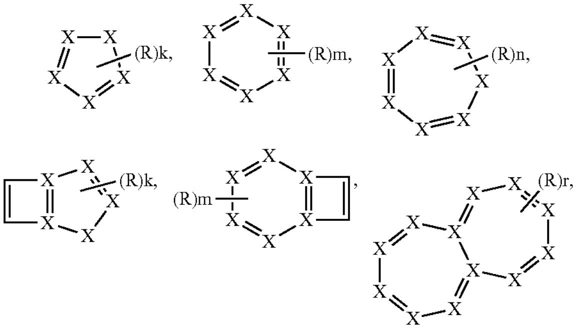
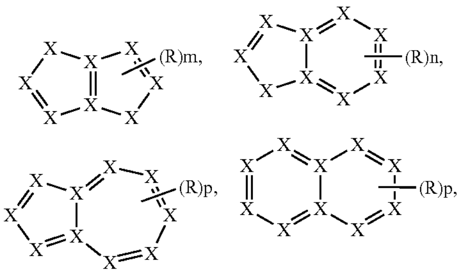

-continued

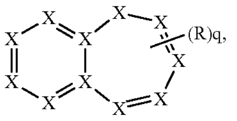
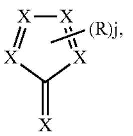
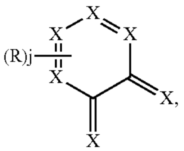
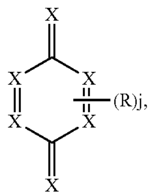
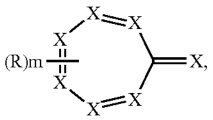
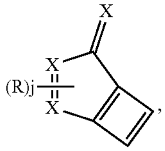
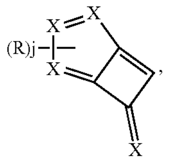
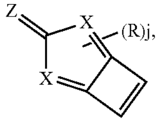
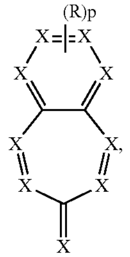
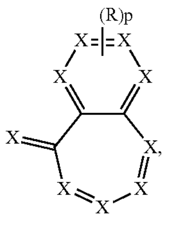
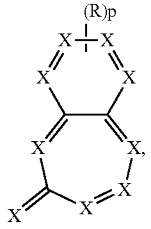
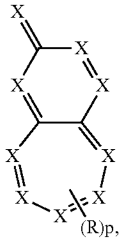
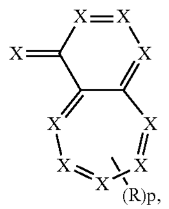
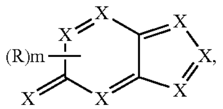
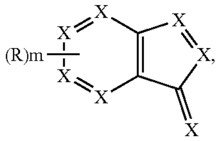
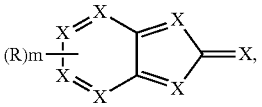
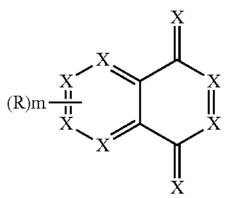

and

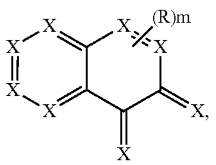

wherein R is independently selected from the group consisting of

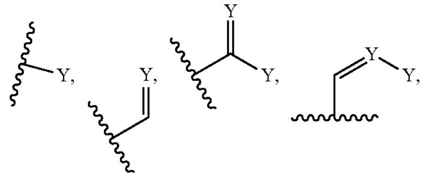
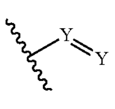

and

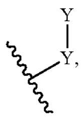

wherein X is independently selected from the group consisting of C, N, O, S, Se, P, and B, wherein at least one X is a C and at least one X is a heteroatom selected from the group consisting of N, O, S, Se, P, and B, wherein Y is independently selected from the group consisting of N, O, S, Se, P, and B, wherein j is selected from 0 to 4, k is selected from 0 to 5, m is selected from 0 to 6, n is selected from 0 to 7, p is selected from 0 to 8, q is selected from 0 to 9, r is selected from 0 to 10, and wherein the moiety is optionally attached to the ligand at any of the carbon atoms.

The R can be attached to the structures shown herein at a carbon or at a heteroatom (N, O, S, Se, P, or B). The monocyclic, bicyclic, hetero- and/or heterobicyclic moieties may be bound to the remaining structure of the ligand molecule by any atom of the cycle or the residue R, which results in a stable structure, optionally by a carbon atom of the moiety.

Optionally two or more of the moieties described herein are interconnected, e.g. via any of the carbon atoms, R or Y, and/or attached to the ligand at any of the carbon atoms or R. Optionally the moiety may comprise a monocyclic aromatic $C_5$-$C_7$ moiety connected to a bicyclic aromatic $C_7$-$C_{12}$ moiety, two interconnected monocyclic aromatic $C_5$-$C_7$ moieties or two interconnected bicyclic aromatic $C_7$-$C_{12}$ moieties, a heteromonocyclic aromatic $C_1$-$C_6$ moiety comprising 1 to 5 heteroatoms connected to a heterobicyclic aromatic $C_2$-$C_{11}$ moiety comprising 1 to 8 heteroatoms, two interconnected heteromonocyclic aromatic $C_1$-$C_6$ moieties comprising 1 to 5 heteroatoms or two interconnected heterobicyclic aromatic $C_2$-$C_{11}$ moieties comprising 1 to 8 heteroatoms. The interconnection may be a direct bond or an interconnection via an atom selected from the group consisting of C, N, O, S, Se, P, and B.

Examples for interconnected heteromono- or heterobicyclic aromatic moieties include, e.g.:

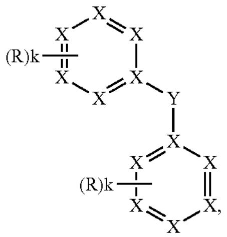
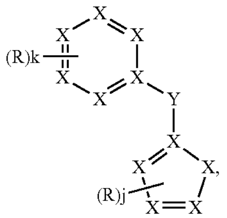

-continued

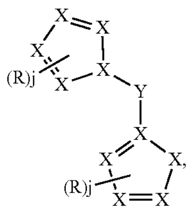

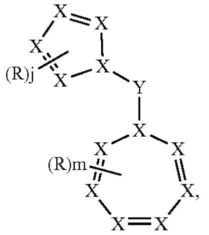

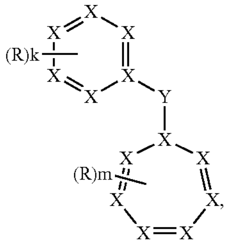

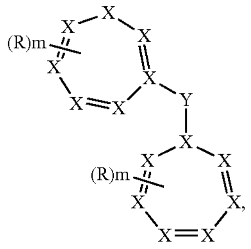

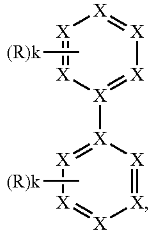

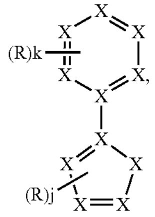

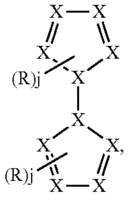

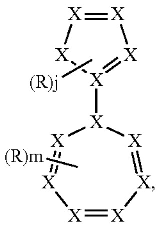

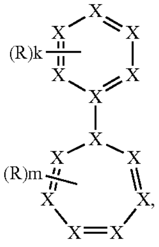

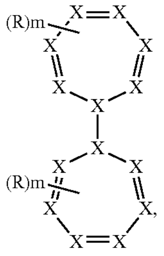

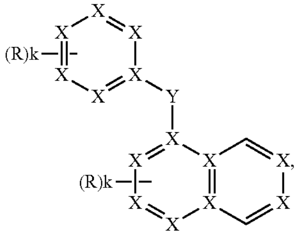

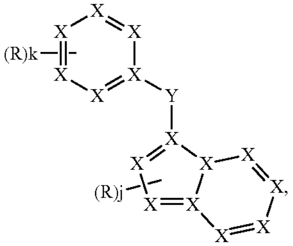

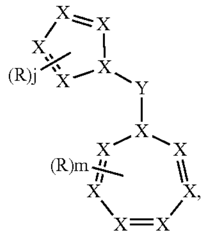

-continued

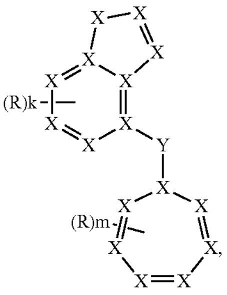

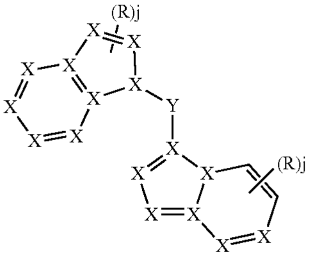

and

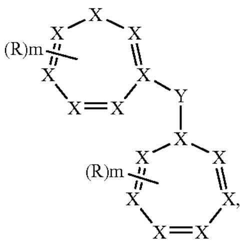

wherein the definitions provided above for the heteromono- or heterobicyclic aromatic moiety structures also apply for these interconnected moieties, wherein the definition that at least one X is a C and at least one X is a heteroatom selected from the group consisting of N, O, S, Se, P, and B optionally applies to the sum of all X atoms per moiety (e.g. to two rings and not to each ring). Optionally the above interconnected heteromono- or heterobicyclic aromatic moieties can be non-heterocyclic or mixed non-heterocyclic and heterocyclic moieties. For non-heterocyclic moieties, the X are C and the remaining definitions provided above apply.

Exemplary chemical entities which the ligand for use in the present invention can comprise include

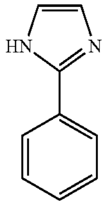

,

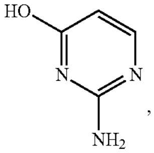

,

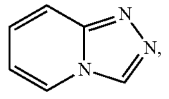

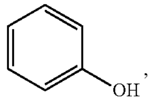

,

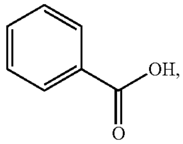

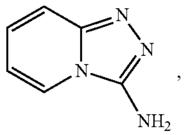

,

-continued

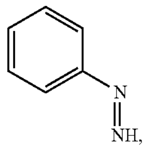
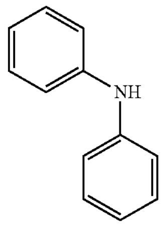
,
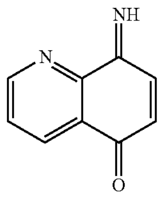
and
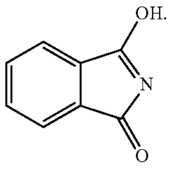

The scope of the present invention includes those analogs of the ligand moieties as described above and in the claims that feature the exchange of one or more carbon-bonded hydrogens, optionally one or more aromatic carbon-bonded hydrogens, with halogen atoms such as F, Cl, or Br, optionally F.

The scope of the present invention also includes those (aromatic) tautomers of the ligand moieties described herein, for example the following tautomers:

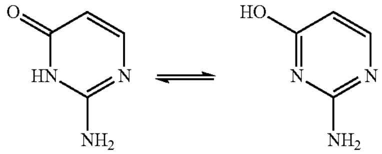
and
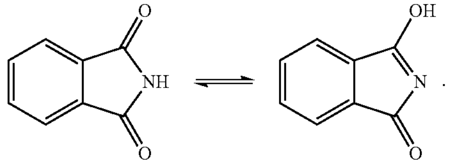

In an embodiment, the ligand to be polarized in the context of this disclosure is or comprises a chemical moiety (entity), wherein the p-orbital of a hetero atom and/or the pi-molecular orbital involving the heteroatom of the ligand or moiety (entity) is/are in resonance (mesomere) with an aromatic ring of the ligand or moiety (entity).

Exemplary chemical entities of the ligand suitable for photochemically induced dynamic nuclear polarization with a photosensitizer include tryptophan, tyrosine, histidine, and indoline.

In an embodiment, the method according to the present invention is one, wherein the ligand or further ligand is a nucleic acid, an amino acid, a (poly-)peptide, optionally a glycopeptide or glycoprotein, optionally a lipoprotein, a mono- or polysaccharide, an antibody, an antibody fragment, a peptidoglycan, a proteoglycan, a terpene, or a small organic molecule.

Exemplary targets include proteins such as, e.g., PIN1 (20 kDa), PDZ domain (10 kDa), αβ-42 and α-synuclein amyloid fibrils, Main protease of SARS-CoV-2 (34 kDa), K-Ras (21 kDa), PGK1 (45 kDa), and *E. coli* thiM TPP riboswitch (82 kDa).

The term "(poly-)peptide" as used herein is meant to comprise peptides, polypeptides, oligopeptides and proteins that comprise two or more amino acids linked covalently through peptide bonds. The term does not refer to a specific length of the product. (Poly-)peptides also include those post-translational modifications of the (poly-)peptides not specifically mentioned, for example, glycosylations, acetylations, phosphorylations, cleavages and the like. The term optionally also encompasses (poly-)peptide analogs, (poly-)peptides comprising non-natural amino acids, peptidomimetics, ß-amino acids, etc.

The term "mono- or polysaccharide" also encompasses oligosaccharides, e.g., those comprising three to ten monosaccharides.

In an embodiment, the method according to the present invention is one, wherein the photosensitizer is selected from the group consisting of flavine, bipyridyl, benzophenone, xanthene, thionine, rhodamine, thiopyronine, benzothiopyronine, oxazine, phenoxazine, acridine, anthraquinone, coumarine, and arylmethine, optionally flavine, xanthene, thionine, thiopyronine, benzothiopyronine and phenoxazine.

In an embodiment, the method according to the present invention is one, wherein the target is selected from the group consisting of a (poly-)peptide, an oligo/polynucleotide, an oligo/polysaccharide, a macromolecular assembly, optionally amyloid fibrils, an organic polymer, and a microporous material, optionally zeolite of metal-organic framework.

Exemplary macromolecular assemblies for use as targets in the present disclosure include amyloids, fibrils, liquid droplets, ribosomes, small nuclear ribonucleoproteins, viral capsids, actine filaments.

Exemplary organic polymers for use as targets in the present disclosure include chitosan, dextrin, polysaccharides, poly (glycolic acid), poly (lactic acid), and hyaluronic acid, (2-hydroxyethyl methacrylate), poly(N-isopropyl acrylamide) s, poly(ethylenimine) s, dendritic polymers.

Exemplary microporous materials for use as targets in the present disclosure include zeolites, metal-organic frameworks.

Exemplary zeolites or metal-organic framework for use as targets in the present disclosure include zeolite-L nanocrystals functionalized or not, chromium-based/copper-based/iron-based/biological metal-organic frameworks.

In an embodiment, the method according to the present invention is one, wherein the NMR spectra in steps (iii), (vi), (x) and (xiv) are Fourier-transformed NMR spectra and the at least one difference in the NMR spectra in steps (vii), (xi) and (xv) is selected from a difference in the area under the curve of a signal, a difference in the intensity of a signal, a difference in the shape of the curve of a signal, a difference in the width of the curve of a signal, a difference in the chemical shift of the signal, and the absence, presence and/or nature of spin couplings.

The absence or presence of at least one difference in the NMR spectra (e.g., in in steps (vii), (xi) and (xv) of the present methods) can relate to the difference in at least one, e.g., isolated, signal or to the difference in the spectrum as a whole, e.g., in the sum of integration over all signals. The comparison of the NMR spectra can be automated, e.g., by any suitable algorithm which detects the presence or absence of a difference and subsequently provides a binary readout, e.g., difference detected or not.

In an embodiment, the method according to the present invention is one, wherein the difference in the intensity of a signal and/or the difference in the area under the curve of a signal is at least √2-fold the noise.

The threshold for the presence of a difference between the NMR spectra is, for example, if the difference spectra obtained, e.g. (iii)-(vi) or (vi)-(x), shows for at least one signal a maximal intensity ($I_{max}$) for which the signal-to-noise value is at least √2-fold the noise of the FT-spectrum (equations (1) and (2)). The signal-to-noise can be calculated using the different built-in functions of the commercially available analysis software. The following exemplary equations can be used to calculate the signal-to-noise ratio (SN). However other suitable equations can be used and are known to the skilled person (Hyberts et al., 2014, J Biomol NMR, Vol. 55, 167-178).

$$SN = \frac{I_{max}}{2 \cdot \text{noise}} \tag{1}$$

And the noise is obtained as follows:

$$\text{noise} = \sqrt{\frac{Y2 - \left(YY + 3XY^2/(N^2-1)\right)/N}{N-1}} \tag{2}$$

And:

$$Y = \sum\nolimits_{i=-n}^{n} y(i)$$

$$Y2 = \sum\nolimits_{i=-n}^{n} y(i)^2$$

$$XY = \sum\nolimits_{i=1}^{n} i(y(i) - y(-i))$$

Where y(i) is the intensity at each interval and YY means Y times Y. The interval i is defined by the skilled person.

Alternatively, the signal and/or sum of signals integrations can be compared for steps (iii) and (vi) or (vi) and (x). The difference between the integrations has to be equal to or greater than √2-fold the noise integration or some of integrations corresponding to the same frequency range.

In the case the desired ligand affinity for the target is defined, the minimal difference can be set from the equations (3) to (8).

Alternatively, in the case where several ligands are screened against a target, the hits can be defined as the ligands for which the difference is significantly above an arbitrary threshold, defined by the skilled person.

In an embodiment, the method according to the present invention is one, wherein an association and/or dissociation constant of the ligand and/or further ligand to the target is calculated based on a decay or accumulation in the nuclear polarization of the ligand in sample (A) and (B), or of the further ligand in sample (B) and (C).

For example, an accumulation or decay in the nuclear polarization of the ligand (L) is determined by repeating each of the steps (ii)/(iii) and (v)/(vi) at least once, wherein a time delay is optionally added between steps (ii) and (iii) and between steps (v) and (vi), optionally a delay (A) from 10 to 5000 ms, wherein the time delay differs in each repetition of the steps (ii)/(iii) and (v)/(vi).

The polarized ligand signal (L*) results from the reversible formation of a radical pair with the dye and is obtained from the steps (ii)/(iii) (sample A, $L_A$*) and/or (v)/(vi) (sample B, $L_B$*). The photosensitizer's concentration (P) remains constant over time, which is a valid assumption as long as irradiation does not exceed the bleaching limit. In the sample (A), all the ligand is free and available for polarization while in sample B the ligand is distributed between free and bound populations such as $L = L_{free} + L_{bound}$, and only the free ligand can be polarized. Two mechanisms are to be accounted, the polarization through photo-CIDNP and the longitudinal relaxation of the magnetization.

$$L_{bound} \rightleftarrows L_{free} \underset{R_1}{\overset{kP}{\rightleftarrows}} L^*$$

The exchange between bound and free ligand populations reaches steady state well before the measurement. In sample (A) there is no such equilibrium and $L_{free}$=L. Therefore, the polarized signal dynamics is modelized according to:

$$\frac{dL^*}{dt} = kPL_{free} - R_1 L^* \tag{3}$$

Where k is the photo-CIDNP reaction rate and $R_1$ the longitudinal relaxation bringing the polarization back to its equilibrium. As the P concentration is considered constant while solving the equation (3), the overall reaction can be approximated by the pseudo-order 1 reaction kinetic:

$$L^* = \frac{kP}{kP + R1} L_{free}\left(1 - e^{-(kP+R_1)t}\right) \tag{4}$$

$L_{free}$ is the concentration of unbound ligand, t is the irradiation time, and k is the reaction rate.

In a second order, the longitudinal relaxation of the signal is considered as the only process taking place, and happens during the delay Δ, and Δ=0 in the case no delay is applied between steps (ii) and (iii) or (v) and (vi). Therefore, the longitudinal relaxation is introduced to the equation (4) to model the polarized signal (L*) obtained from the application of steps (ii)/(iii) (sample A, $L_A$*) and/or (v)/(vi) (sample B, $L_B$*) is to first order given by:

$$L^* = \frac{kP}{kP + R_1} L_{free}\left(1 - e^{-(kP+R_1)t}\right) e^{-R_1 \Delta} \tag{5}$$

In the fast exchange limit, the longitudinal relaxation of the ligand is the average between its free form ($R_{1,L}$) and bound ($R_{1,LT}$) form relaxation rates:

$$R_1 = R_{1,L}\frac{L_{free}}{L} + R_{1,LT}\frac{L_{bound}}{L}.$$

The value of the average relaxation rate can be obtained from state-of-the-art inversion recovery experiments, with or without photo-CIDNP. It is noted that the bound form relaxation rate is similar to the target relaxation rate.

Since only $L_{free}$ is considered to be polarizable through the reaction with the photosensitizer, the proportion of free ligand and bound ligand ($\alpha = L_{bound}/L$, and $1-\alpha = L_{free}/L$) among L is defined as follows:

$$\alpha = \frac{L + T + K_d - \sqrt{(L + T + K_d)^2 - 4LT}}{2L} \tag{6}$$

Where L and T are the total ligand and target concentrations, respectively, and $K_d$ is the dissociation constant of the target-ligand complex.

The polarized signals intensities and/or integrals of the sample A ($L_A$*, steps (ii)/(iii)) and sample B ($L_B$*, steps (v)/(vi)) are combined into a ratio to obtain equation (7):

$$\frac{L_B^*}{L_A^*} = \frac{kP + R_{1,A}}{kP + R_{1,B}} \frac{1 - e^{-(kP+R_{1,B})t}}{1 - e^{-(kP+R_{1,A})t}} [1 - \alpha] e^{-(R_{1,A} - R_{1,B})\Delta} \quad (7)$$

The equation (7) can be titrated by repeating steps (ii)/(iii) and (v)/(vi) with different irradiation time (t) or delays (4) or ligand (L) or target (T) amounts. The delay (Δ) can be kept equal to 0 to simplify equation (7). The $R_{1,A}$ and $R_{1,B}$ are the relaxation rates for the samples A and B, and alternatively, the estimations of the relaxation rates can be used. Furthermore, if the irradiation time t is kept short the exponent can be neglected yielding an estimation of the Kd in two single experiments. The ratio obtained, $$\left(\frac{L_B^*}{L_A^*} = \frac{(v)/(vi)}{(ii)/(iii)}\right),$$

is used to fit equation (7) for the appropriate $K_d$. Alternatively, for irradiation times well below $1/R_{1,LT}$, typically <100-200 ms, and with delay (Δ) equal to 0, the exponential terms in the equation (7) term can be approximated to 1, so the that signal ratio is proportional to (1−α). Hence, this initial quasi linear regime can be used to obtained the $K_d$. The choice of using the linear regime or the non-linear regime conditions, i.e., irradiation times>>200 ms) is made by the skill person, according to the experimental conditions.

In the case of a further ligand ($L_2$, sample C, step (ix)/(x)), the term a needs to be replaced in equation (7) to obtain an exact analytical solution. Only the dissociation constant of the competing ligand $K_{d,2}$ is fitted, as $K_{d,1}$, the dissociation constant of the displaced ligand ($L_1$) is known. In this case the ratio to measure is $$\frac{L_C^*}{L_A^*} = \frac{(ix)/(x)}{(ii)/(iii)},$$

and is later fitted to equation (7) with α defined in (8) to find the relevant $K_{d,2}$ (the dissociation constant of the further ligand, $L_2$).

$$\alpha = \frac{\left\{2\sqrt{a^2 - 3b}\cos\left(\frac{\theta}{3}\right) - a\right\}}{3K_{d,1} + \left\{2\sqrt{a^2 - 3b}\cos\left(\frac{\theta}{3}\right) - a\right\}} \quad (8)$$

Where:

$$\theta = \sin^{-1}\left(\frac{-2a^3 + 9ab - 27c}{2\sqrt{(a^2 - 3b)^3}}\right)$$

And:

$$a = K_{d,1} + K_{d,2} + L_1 + L_2 - T$$

-continued $$b = K_{d,2}(L_1 - T) + K_{d,1}(L_2 - T) + K_{d,1}K_{d,2}$$

$$c = -K_{d,1}K_{d,2}T$$

The demonstration for the analytical solution of a competitive experiment is known in the art (see, e.g., Wang, FEBS letter, 1995, Vol 360, p. 111-114). The competitive binding can of course also be solved numerically based on the radioligand competitive assays equations.

In another aspect, the present invention is directed to a method for determining the structure of a ligand-target complex, the method comprising the following steps:

(I) optionally determining and/or characterizing a ligand-target binding according to the method for detecting and/or characterizing a ligand-target binding based on photochemically induced dynamic nuclear polarization (photo-CIDNP) enhanced NMR spectroscopy as described herein;

(II) providing a sample comprising a ligand bound to a target and a photosensitizer, optionally sample (B) as described herein, wherein the photosensitizer is suitable for chemically inducing dynamic nuclear polarization of the ligand upon irradiation of the sample;

(III) irradiating the sample at a wavelength and duration suitable for exciting the photosensitizer and under conditions allowing for chemically induced dynamic nuclear polarization of the ligand by the photosensitizer;

(IV) recording a nuclear Overhauser effect (NOE) 2D NMR spectrum;

(V) determining the structure of the ligand-target complex based on the NOE 2D NMR spectrum.

Figure 4:
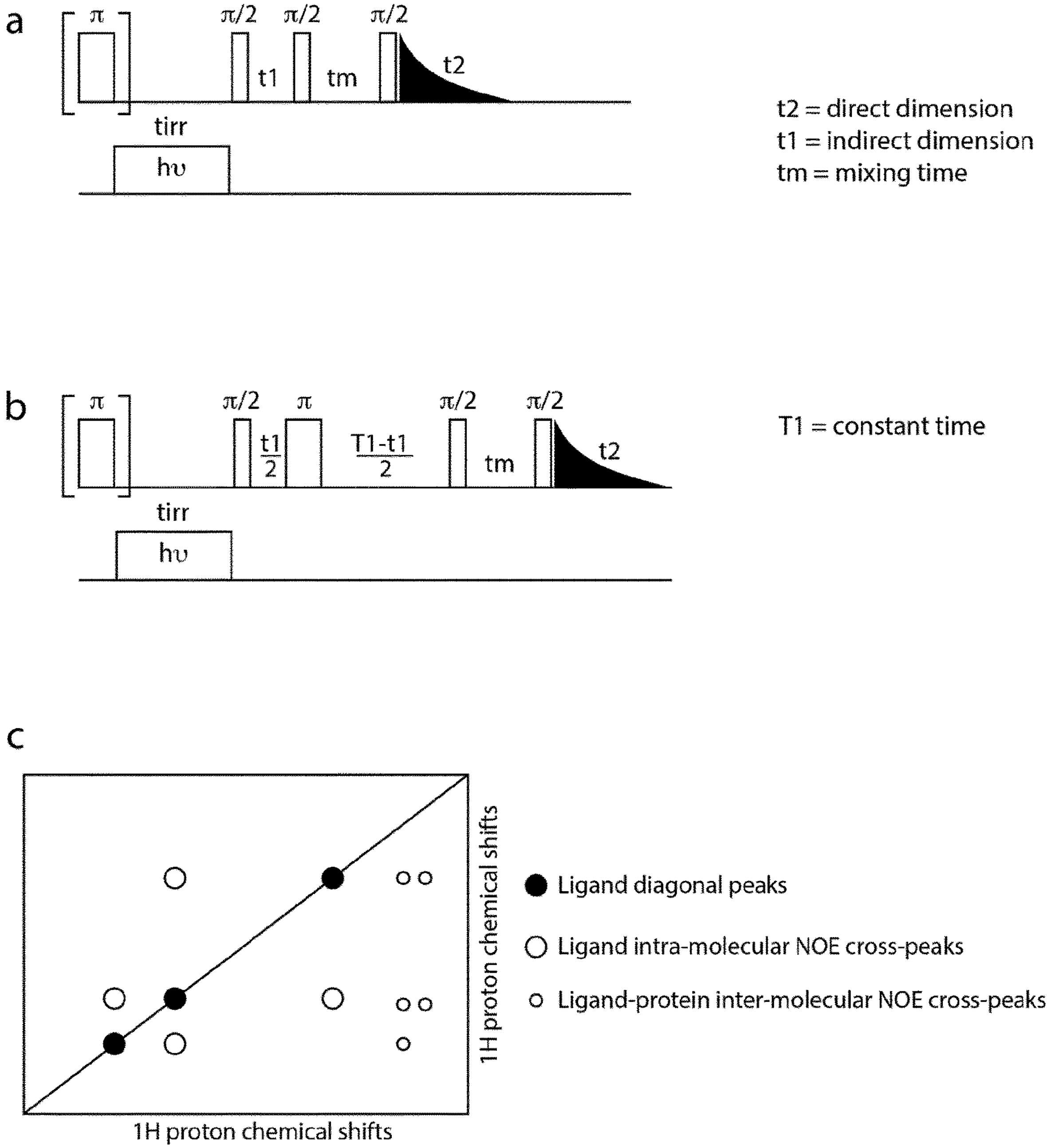

The 2D, e.g., NOESY, NMR spectrum recorded in the present method can be recorded with single or multiple scans for the direct dimension corresponding to the FID acquisition (with a typical t2=100 ms to 1000 ms). The irradiation is repeated at each scan, for a delay ranging from, e.g., 0.1 to 5 s. The second dimension of the spectrum is obtained by repeating the measurement of direct dimension of pulse sequence as described in FIG. 4, and varying the delay t1, providing the indirect dimension. The indirect dimension is recorded for different delays t1 varying from, e.g., 0 ms to t1max, with t1max=6 ms to 50 ms. The indirect dimension can optionally be recorded using a constant time indirect time evolution pulse scheme (FIG. 4*b*), where T1=t1max. The phase of the radio frequency pulses can be optionally evolved for each indirect time evolution increment according to the different acquisition modes (QSEQ, STATES, STATES-TPPI, TPPI). The mixing time (tm) can be chosen with values ranging from, e.g., 10 ms to 250 ms. A further option is to apply a 180° pulse (π) prior to the light irradiation. Due to the chemically induced dynamic nuclear polarization of the ligand, the time required for acquiring 2D spectra, e.g., NOESY spectra, in the present method are comparatively short, e.g., ranging from 45 mins to 1.5 h (compared to regular, non-polarized NOESY acquisitions which take about 24 h). Furthermore, because of the chemically induced dynamic nuclear polarization of the ligand, the target signal does not need to be filtered due to the ligand's signal being significantly higher, e.g., more than an order of magnitude higher, than that of the target. And because of the ligand polarization along with potential $T_2$ and $T_1$ filters, the target does not need to be labeled.

Of course, other 2D NMR methods, e.g., spin-diffusion experiments or NOESY-HSQC can be used for determining the structure of a ligand-target complex in the context of the present method. It is within the purview of the skilled person to determine a structure from the data obtained by one of these 2D NMR methods.

In another aspect, the present invention is directed to a device (1) for conducting any of the methods described herein, the device comprising:

(a) a sample holder (2), optionally a multi-well plate, wherein the sample holder, optionally each well, has a bottom (2*a*) and a top (2*b*) and comprises sample (A) or (D) and (B) or (C) as described herein;

(b) an NMR device (3) comprising a sample tube (4) and a light-emitting device (5), wherein the sample tube (4) is in fluid communication with the sample holder (2) and the light-emitting device (5) is configured to irradiate and excite the photosensitizer allowing for chemically induced dynamic nuclear polarization of the ligand in the sample in the sample tube (4) within the NMR device (3);

(c) a pump (6) configured to move a sample from the sample holder (2) to the sample tube (4); and (d) at least one processing unit (7) configured to (d1) synchronize the movement of the sample from the sample holder (2) to the sample tube (4) with a measurement operation of the NMR device (3) and optionally with the irradiation of the light-emitting device (5); and optionally at least one of (d2) compare the NMR spectra obtained according to the method for detecting and/or characterizing a ligand-target binding based on photochemically induced dynamic nuclear polarization (photo-CIDNP) enhanced NMR spectroscopy as described herein;

(d3) detect and/or characterize a ligand-target binding according to the method for detecting and/or characterizing a ligand-target binding based on photochemically induced dynamic nuclear polarization (photo-CIDNP) enhanced NMR spectroscopy as described herein;

(d4) calculate an association constant according to the method described herein; and/or (d5) determine and provide structural data of a ligand-target complex according to the method for determining the structure of a ligand-target complex as described herein.

The sample holder can be any device suitable for (e.g., temporarily) storing a sample, such as a liquid. The sample holder typically comprises the samples used in the method disclosed herein, e.g., Samples (A), (B), (C) and/or (D). The sample holder may be accessed, e.g., to draw a sample, from the bottom and/or top of the sample holder, and the sample holder may be a multi-well plate or consist of individual sample vials.

The light-emitting device in the NMR device may be any device that is suitable for emitting the (light) irradiation used in the method disclosed herein. For example, the light-emitting device may be an optic fiber which is connected to a further light-generating device, e.g., positioned outside the NMR device, such as LASER, LED, OLED, gas discharge lamps or incandescent lamps.

The NMR device of the present device may be any NMR spectrometer suitable for recording 1D or 2D spectra of the nuclei disclosed herein in the context of the present method. For example, it may be a 0.9 T magnet up to a 28.2 T magnet.

The sample tube may be any device suitable for temporarily positioning a sample, e.g., a liquid sample as disclosed above, in the NMR device, e.g., a flexible tube that is permeable to the irradiation from the light-emitting device, at least at those wavelengths required for the irradiation in the context of the present method. Exemplary sample tubes also include standard NMR glass vials/tubes. For example, a syringe or a (flexible, e.g., hose-like) tube may be used to collect a sample from the sample holder and a (further, e.g., flexible) tube may be used to move the sample into the NMR device, wherein the same tube may constitute the sample holder. For example, tubes used in standard HPLC devices may be used as tubing and/or sample tube. Further and specific sample tubes (e.g. 4*a*, 4*b* and 4*c*) are described below.

Any device suitable for moving a liquid from the sample holder to and optionally through the sample tube can be used as a pump in the context of the present device. For example, a (e.g. peristaltic) pump used in HPLC devices may be used.

The processing unit may be a single unit or it may comprise several processing (sub-) units, each of which may perform one or multiple of the tasks described herein. The task of synchronizing the movement of the sample from the sample holder (2) to the sample tube (4) may also include sample selection, and optional valve movement.

At least one of the processing units processes the NMR acquisition data, i.e. "performs" the NMR measurement (incl. radio pulses, optional spin lock, etc.) and displays the measured data. At least one of the processing units essentially performs at least parts of the method according to the present invention, i.e., the steps (iii), (vi), (vii) at least partially, (x), (xi) at least partially, (xiv), (xv) at least partially, (V), and optionally (V). "At least partially" for the relevant method steps means that the processing unit at least displays the data of the NMR measurement, e.g., the FID or the FT-spectrum, e.g. in a (visual) fashion which allows for comparison of at least two spectra. The processing unit may optionally also, e.g., automatically, detect and/or characterize a (competitive) binding of the (further) ligand to the target based on the presence or absence of at least one difference in the NMR spectra, optionally calculate an association constant as described herein and/or optionally determine and provide structural data of a ligand-target complex as described herein.

In an embodiment, the device of the present method is one, wherein the device (1) is configured for continuous sample measurement by continuous batch-wise movement of samples from the sample holder (2) to the sample tube (4), and/or each of steps (d1) to (d5) are performed by one or individual control unit(s) (7).

Continuous or batch-wise movement of the samples refers to the samples as described herein, e.g., any of samples (A), (B), (C) and/or (D). Batch-wise movement of samples through tubes is known in the art of analytical chemistry and requires no further explanations for the skilled person. The continuous or batch-wise movement of the samples through the device of the invention allows for a screening, e.g., a high-throughput screening, of samples for detecting and/or characterizing a ligand-target binding according to the present method.

The device optionally further comprises suitable sources for drawing solvent (e.g., the solvent of the samples) and/or purging liquids which may be administered to the tubing of the device, e.g., under the control of the pump or optional valves. The sample, solvent(s) and/or purging liquids may be disposed to a waste container (12), e.g. from the sample tube (4).

An exemplary device of the present invention is described with reference to FIG. 3: The device (1) comprises a sample holder (2) which, e.g., comprises a sample of interest for detecting and/or characterizing a ligand-target binding based on the method disclosed herein. The sample holder (2) can be accessed, e.g., from a top (2*b*) of the sample holder, e.g., by a syringe or a tube suitable for drawing the sample from the sample holder (2). Alternatively or additionally, the sample may be placed into or drawn from the sample holder (2) from its bottom (2*a*), e.g. through a membrane or a closable/removable lid (not shown). The sample is then delivered to the sample tube (4) positioned within the NMR device (3), e.g., through a tube which is in fluid communication with the syringe or tube which was used to draw the sample from the sample holder (2). To move the sample through the device, a pump (6) can be used. The flow may be controlled by pump operation or by valves located within the tubing of the device. All of these may be controlled by the processing unit (7). For example, during the recording of an NMR spectrum, a solvent, e.g., the solvent of the samples, may still be moved through the tubing connecting the site of sample drawing and the pump and an optional valve may direct this solvent flow away from the tubing which leads to the sample tube (4), e.g., to waste (12). Optionally, an autosampler may be used with different ports and valves configured to draw and move individual samples from the sample holder (2) to the sample tube (4), which mechanism may also be controlled by the processing unit (7). Alternatively, the sample may be transferred to the sample tube (4) by any means of transfer suitable for placing the sample in the sample tube (4), for example, by pipetting optionally by hand. The term "in fluid communication" encompasses the option that the sample is moved from a sample holder (2) or any other container comprising the sample to the sample tube (4) by hand, e.g. via pipetting. For example, the processing unit (7) may instruct an operator on when and/or how to manually transfer the sample (e.g. by pipetting) to the sample tube (4), e.g. in order to synchronize the movement of the sample with the measurement operation of the NMR device (3) and optionally with the irradiation of the light emitting device (5). Alternatively, the processing unit (7) may instruct the user or any commercially available auto sampling device to change the sample tube (4). In the latter case, the sample would have been previously transferred to the sample tube (4) and stored accordingly. The light-emitting device (5) is positioned such that it is suitable for emitting the (light) irradiation used in the method disclosed herein onto the sample in the sample tube, optionally via the inner tube (9) as detailed below. For example, the light-emitting device (5) may be an optic fiber which is connected to a further light-generating device (8), e.g., positioned outside the NMR device and which light-emitting device (5) is positioned such that it specifically irradiates the sample which is to undergo an NMR measurement. After measurement, the sample may be recollected or disposed as waste. Although only one processing unit (7) is shown, the device (1) may comprise more than one processing units (7), each of which may have different tasks (as described above).

In an embodiment the device of the present invention is one, wherein the sample tube (4) is in the form of a coaxial sample tube (4*a*, 4*b*, 4*c*) comprising an inner tube (9) having a top and a bottom positioned within an outer tube (10) having a top and a closed bottom and configured to receive the sample.

The inner tube (9) can be made of any material and shape suitable to be inserted into the outer tube (10). It may be hollow or solid and may be made of, e.g. plastic, glass or quartz and it may be transparent or comprise non-transparent parts. The inner tube (9) may have a closed bottom or comprise an opening, e.g. in the bottom, to allow a sample to pass from the inner tube (9) to the outer tube (10). If the inner tube (9) is solid, the sample may be added to the outer tube (10), e.g. from the top of the (open) outer tube (10). Alternatively, if the inner tube (9) is solid, it may comprise a channel to admit the sample, e.g. from the sample holder (2), through the inner tube (9) to the outer tube (10).

The outer tube (10) is suitable for receiving and for storing the sample at least temporarily for the duration of NMR spectra recording, e.g. in fluid form as described herein (e.g. stopped-flow). In essence, the sample will be located between the inner surface of the outer tube (10) and the outer surface of the inner tube (9). It may be made of, e.g. plastic, glass, quartz or (non-ferromagnetic) metal and it may be transparent or non-transparent.

The outer tube (10) may optionally be in fluid communication with a waste container (12), e.g. via the top of the outer tube (10).

In an embodiment the device of the present invention is one, wherein the inner tube (9) comprises an inlet tubing (11) configured to transfer a sample from the sample holder (2) through the inner tube (9) to the outer tube (10).

The inlet tubing (11) can be, e.g. an HPLC tubing or any other tube or tubing suitable for transporting a (e.g. liquid) sample from the sample holder through the inner tube (9) to the outer tube (10). The inner tube may have an opening in the top or an open top into which the inlet tubing is inserted and, e.g. a hole, e.g. in or near the bottom, through which the inlet tubing (11) ends or protrudes to admit the sample into the space between the outer surface of the inner tube (9) and the inner surface of the outer tube (10). The inlet tubing (11) is sealed against the inner volume of the inner tube (9) so that the sample does not reach the inner volume of the inner tube (9). Alternatively, the inner tube (9) may comprise a channel suitable for transporting a (e.g. liquid) sample from the sample holder through the inner tube (9) to the outer tube (10). For example, the inner tube (9) may be a solid, e.g. glass, structure, e.g. in the shape of a test tube or finger, comprising the channel.

The light emitting device (5) may be positioned within the inner tube (9) or it may be positioned outside the inner tube (9) and the inner tube (9) may be used as an optical guide to transfer light for irradiation, e.g. from the top of the sample tube, to the sample.

In an embodiment the device of the present invention is one, wherein the inner tube (9)

i. comprises the light emitting device (5),
ii. comprises a buffer, optionally deuterated water, and/or
iii. has an etched inner and/or outer surface, optionally at the location of an NMR radiofrequency coil of the NMR device (3).

The etched surface at the location of the NMR radiofrequency coil can improve the light-sample coupling.

In another aspect, the present invention is directed to a use of any of the method described herein or the device as described herein for detecting and/or characterizing a ligand-target binding, optionally a competitive ligand-target binding, for calculating an association constant of a ligand to a target, and/or for determining a structure of a ligand-target complex.

The following, Figures and Examples serve to illustrate the invention and are not intended to limit the scope of the invention as described in the appended claims.

FIG. 1: shows a schematic and exemplary representation of the indicated method steps according to the present invention with samples (A), (B), (C) and (D) with schematic NMR FT-signals. L=ligand, P=photosensitizer, T=target, F=further ligand. The NMR spectrum of sample (A) in step (iii) can be used as a reference (e.g., FT-)spectrum represented by a schematic peak, which may also correspond to the sum of all peaks or to any specific signal characteristic as disclosed herein (the same holds true for all signals of FIG. 1). For sample (B) in step (vi) two cases are shown: one in which there is no interaction (no binding) between the ligand and the target (vi.a) and a scenario in which there is an interaction (binding, vi.b). The respective NMR signals are then subtracted from the signal of sample (A) and in the case of binding (vi.b), there is a difference in the NMR signal (spectrum) which is indicative of ligand-target binding. Of course, any type of comparison is suitable; addition of the signal would also be possible and subtraction is shown for easier representation. For the further ligand (e.g. a potential competitive binder) of sample (C) the signal of step (vi.b) is compared to that of step (x) and the difference in the signals is indicative of competitive binding (vi.b-x.b). On the other hand, if the difference between the signals was zero, this would be indicative of no interaction (no binding). The step of validating the detection and/or characterization of the competitive binding of the further ligand to the target is shown for sample (D), wherein the absence of a difference in the NMR spectra of steps (iii) and (xiv) validates the detection and/or characterization of the competitive binding of the further ligand to the target, e.g. by excluding an interaction between the ligand and the further ligand.

FIG. 2 *a*) shows an exemplary and non-limiting pulse sequence for use in a method according to the present invention. $\pi/2$ is a 90° radio frequency pulse, $\phi$ is the phase of the pulse (e.g. x for sample (A) and −x for sample (B)), tirr is the irradiation time, hv symbolizes light irradiation, SL is a spin lock (e.g. up to 105 kHz) and $\gamma$ is the phase of the spin lock (e.g. y for sample (A) and −y for sample (B)). FIG. 2*b*) shows the NMR spectra of Example 2 and FIG. 2*c*) shows a plotting of the difference in the spectra to visualize the 'hits' molecules. FIG. 2*d*) a) shows the signal-to-noise enhancements of peptide 1 resonance at 7.4 ppm for the samples A and samples B-I to B-IX at different irradiation time (step (ii)). b) shows the $L_{bound}/L$ at different PDZ protein domain concentrations.

Figure 3:
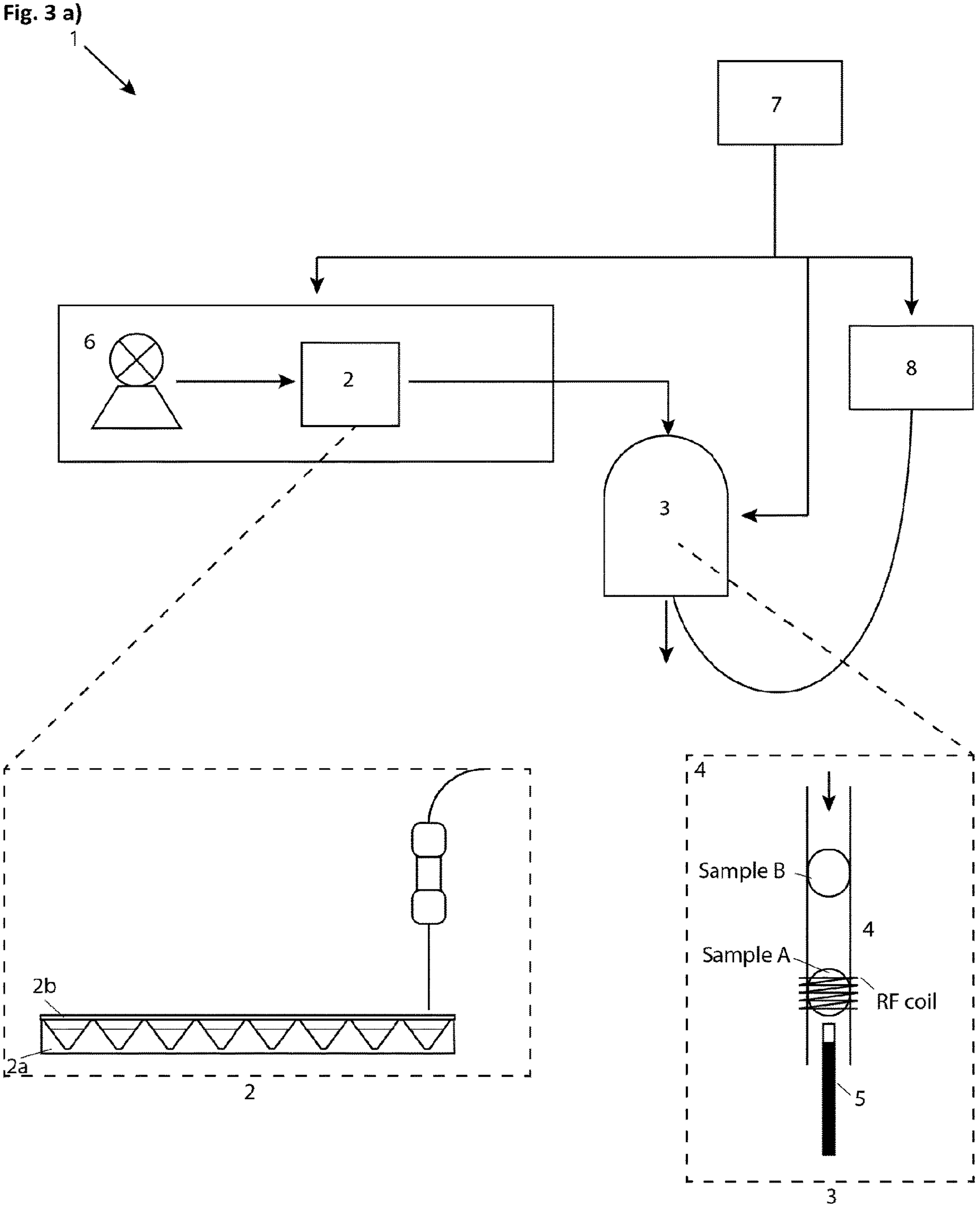
Figure 3:
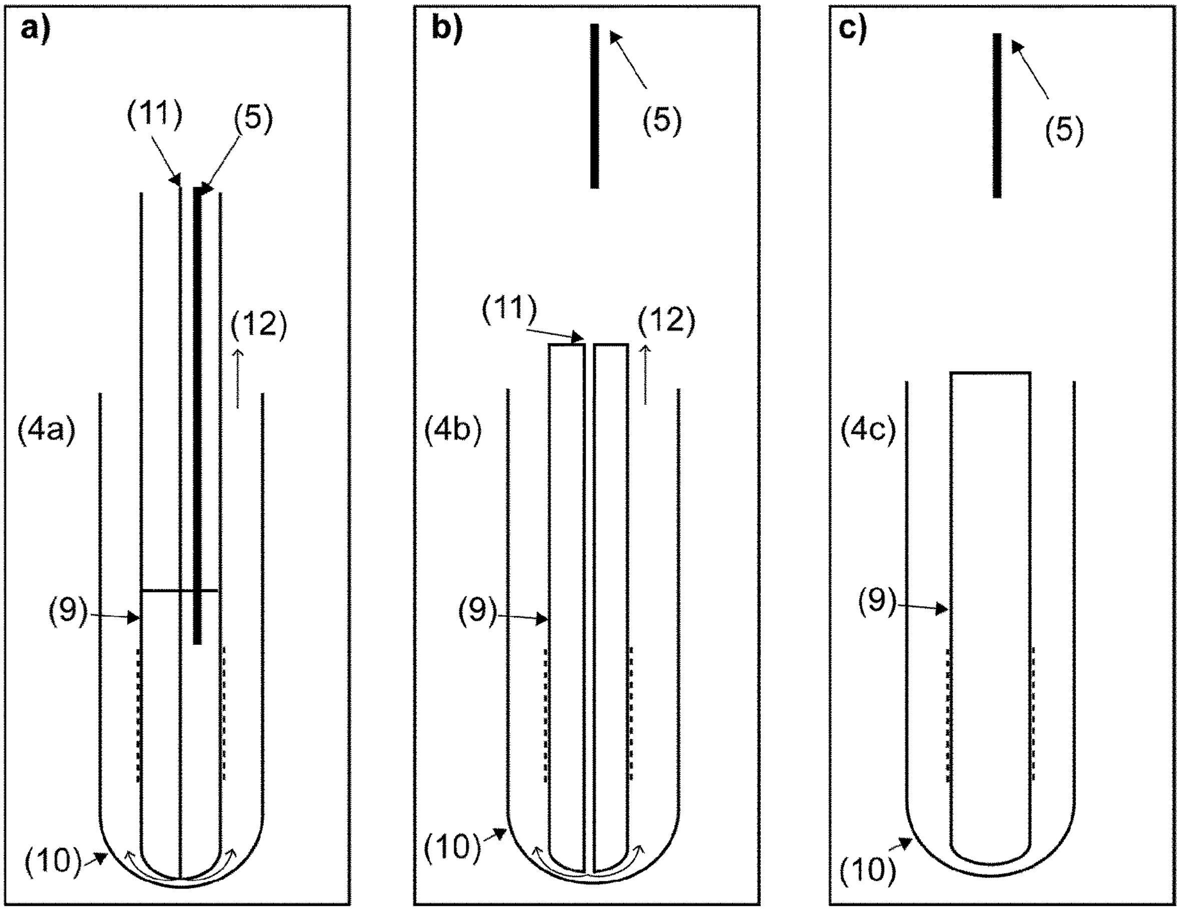

FIG. 3 *a*) shows an exemplary device (1) according to the present invention which is detailed above.

FIG. 3*b*) a) shows a sample tube (4*a*) comprising a coaxial tubing, with the inner tube (9) comprising the inlet coming from the sample holder (2), e.g. in the form of an inlet tubing (11), e.g. an HPLC tubing, reaching through the inner tube (9) and configured to deliver the sample into the space between the outer surface of the inner tube (9) and the inner surface of an outer tube (10). The sample tube (4*a*), may also comprise the light emitting device (5) within the inner tube (9), and an optional buffer, optionally deuterated water. The inner tube (9) can be made of any suitable material, e.g. glass, quartz, or plastic and is preferably at least partially transparent to allow for light to reach the sample contained in the outer tube (10). The outer tube (10) is configured as a container and receives/comprises the sample transferred from the sample holder (2) via the inlet tubing (11). The sample is therefore contained in the wall of the coaxial tubing, i.e., in the space between the inner tube (9) and the outer tube (10). Optionally, the inner and/or outer surface of the inner tube (9) can be etched (dashed lines) at the location of the NMR radiofrequency coil to improve the light-sample coupling. The sample can be washed and evacuated to the waste (12) by pushing buffer through the inlet tubing (11). FIG. 3*b*) b) shows an inner tube (9) in the form of a solid tube or stick with an opening or channel forming the inlet tubing (11) configured to transfer a sample from the sample holder to the outer tube (10). The outer tube (10) is configured as a container and receives/comprises the sample transferred from the sample holder (2) and entering by the inlet tubing (11). The sample is therefore contained in the wall of the coaxial tubing, i.e., the space between the inner tube (9) and the outer tube (10). The inner tube (9) is used as an optic guide to transfer the light that is shined, e.g. from the top of the spectrometer, by the light emitting device (5). The inner tube (9) can be of an optically transparent material, e.g., glass or quartz. Optionally, the inner and/or outer surface of the inner tube (9) can be etched (dashed lines) at the location of the NMR radiofrequency coil to improve the light-sample coupling. FIG. 3*b*) c) shows the outer tube (10) containing an inner tube (9) which is made of optically transparent material, e.g., glass or quartz and forms an, optionally solid, tube, stick or finger reaching close to or to the bottom of the outer tube (10). The sample is therefore contained in the wall of the coaxial tubing, i.e., the space between the inner tube (9) and the outer tube (10). The inner tube (9) is used as an optic guide to transfer the light that is shined from the top of the spectrometer by the light emitting device (5). Optionally, the inner and/or outer surface of the inner tube (9) can be etched at the location of the NMR radiofrequency coil (dashed lines) to improve the light-sample coupling. For all sample tubes (4*a*, 4*b* and 4*c*), the relative positions shown for the inner and outer tubes (9, 10), e.g. how far down the inner tube (9) reaches or how large/small the distance from the wall of the inner to the wall of the outer tube is, is not limiting and any relative position is within the scope of this disclosure as long as the sample transfer and/or light transfer can be achieved in the context of the method described herein.

FIG. 4*a*-*b*) shows exemplary pulse and delay sequences of a 2D, e.g., NOESY, NMR spectrum recorded according to the present method. tirr is the irradiation time, hv symbolizes light, $\pi/2$ is a 90° radio frequency pulse and $\pi$ is a 180° radio frequency pulse. Square brackets indicate an optional radio frequency pulse. FIG. 4*c*) shows an exemplary 2D, e.g., NOESY, $^1$H-NMR spectrum obtained with the ligand diagonal peaks (solid dots) intra-(larger sized empty dots) and inter-molecular (smaller sized empty dots) cross-peaks.

Figure 5:
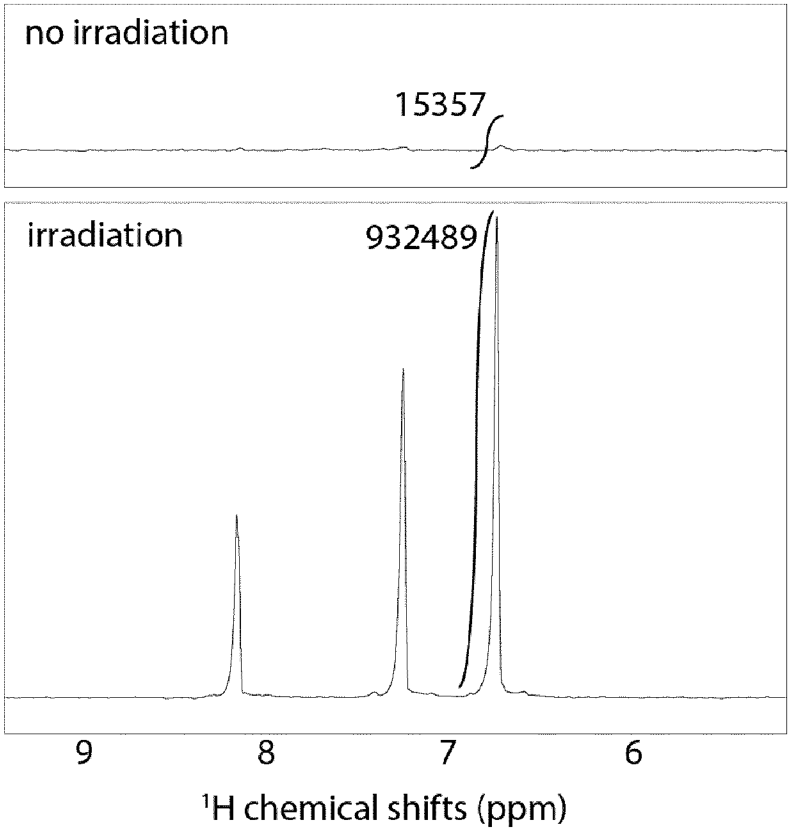

FIG. 5 shows the 1D $^1$H NMR spectra of tofacitinib (100 μM) not preceded (step (iii), top) and preceded by irradiation (step (ii)/(iii), bottom) in the presence of fluorescein (25 μM) as described in Example 1.

Figure 6:
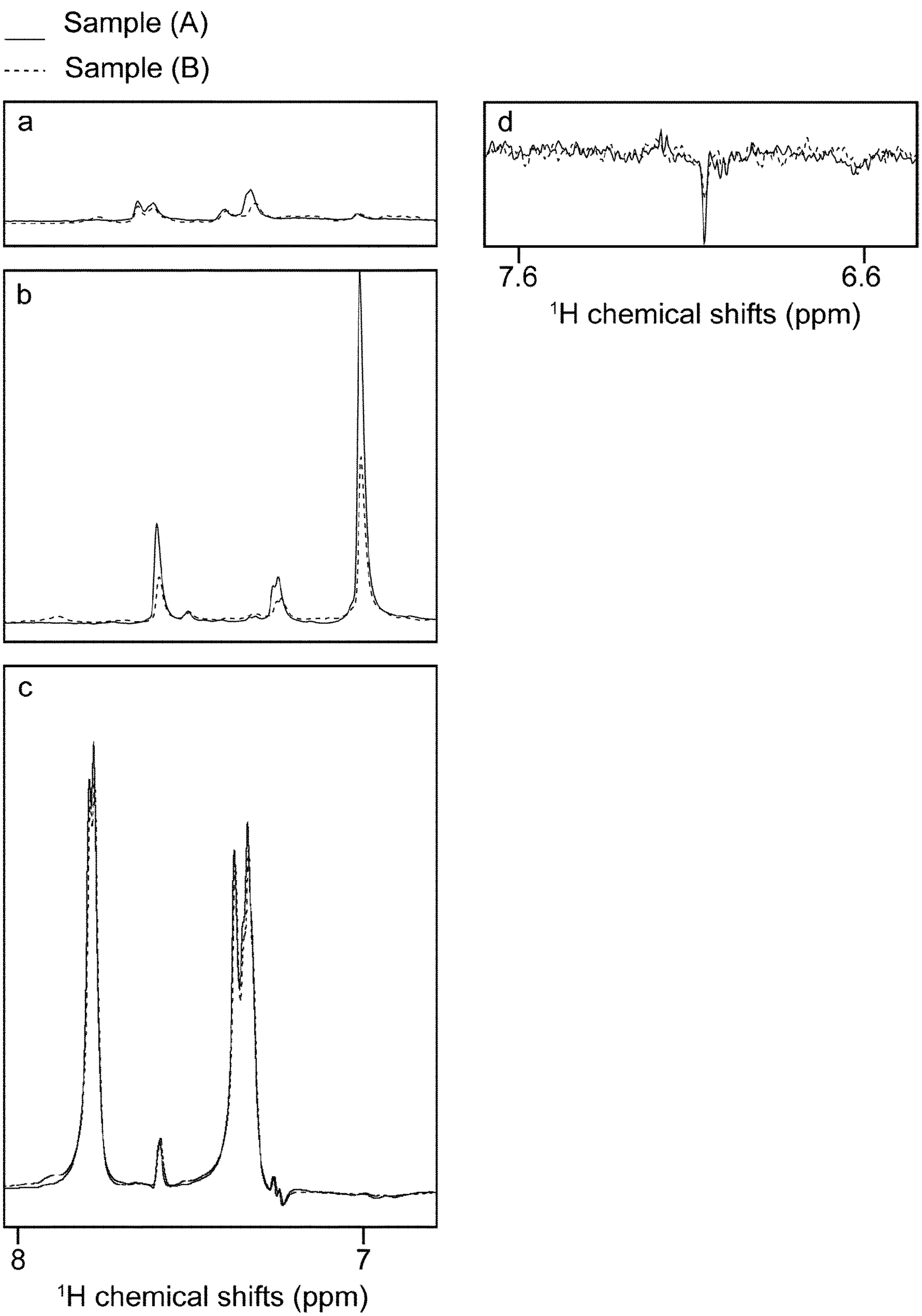

FIG. 6 shows the 1D $^1$H NMR spectra of ligand 3-1 (5-methyl-2-(3-methylphenyl)-imidazole-4-carboxylic acid, FIG. 6*a*), ligand 3-2 (5-methyl-indole-3-carboxylic acid, FIG. 6*b*), ligand 3-3 (tryptophan, FIG. 6*c*) and ligand 3-4 (4-hydroxy-8-oxa-11-azatricyclo[7.5.0.0$^{2,7}$]tetradeca-1 (9), 2,4,6-tetraen-10-one, FIG. 6*d*) recorded together with PIN1 protein as target according to Example 3. Solid lines refer to sample (A) (ligand without target) and dashed lines refer to sample (B) (ligand plus target).

Figure 7:
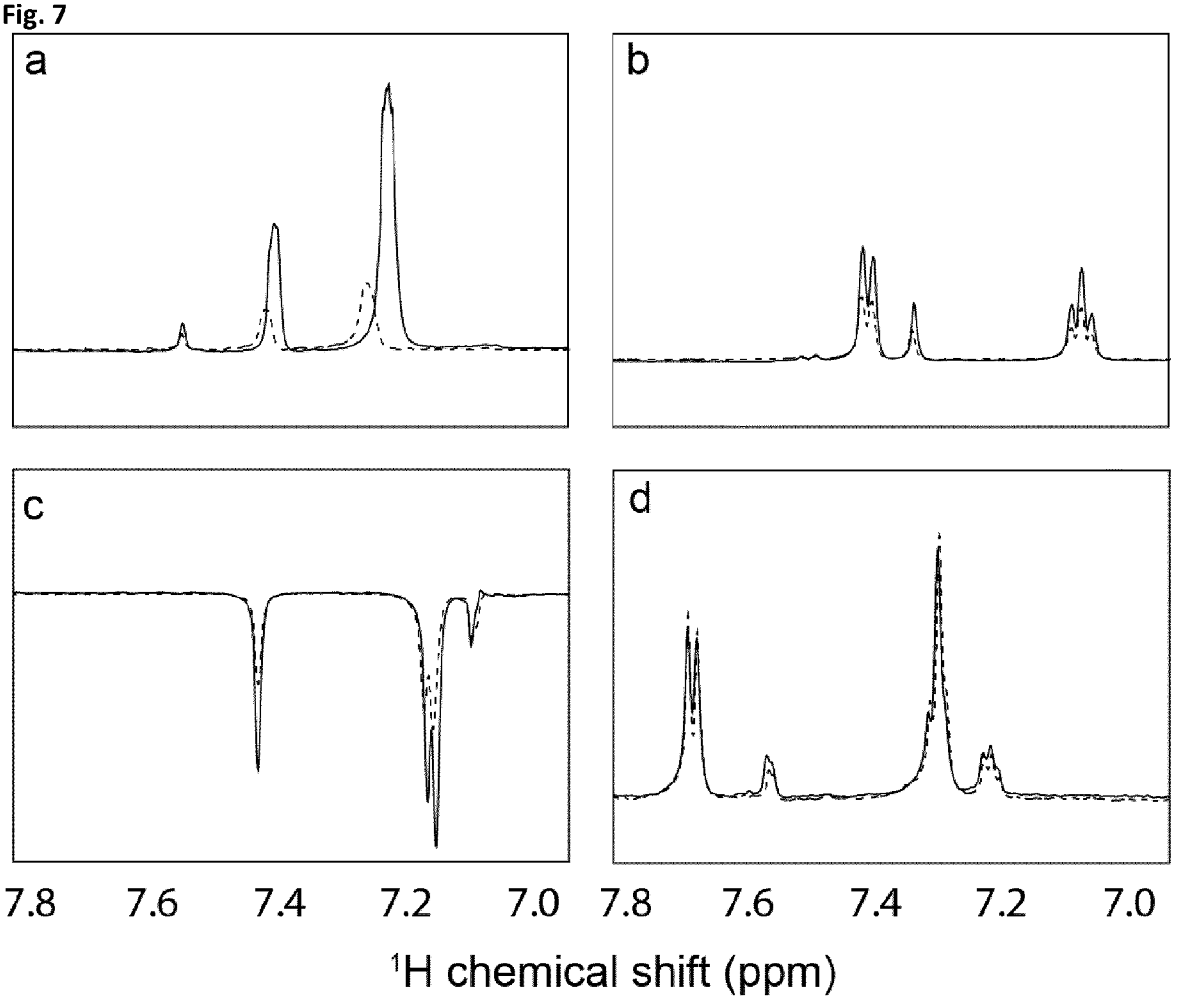

FIG. 7 shows the 1D $^1$H NMR spectra of ligand 4-1 (5 N-(Furan-2-ylmethyl)-1H-benzimidazol-2-amine)-imidazole-4-carboxylic acid, FIG. 7*a*), ligand 4-2 (N-[2-(5-fluoro-1H-indol-3-yl)ethyl]acetamide, FIG. 7*b*), ligand 4-3 (N-(2-methoxy-5-methylphenyl)-N'-4H-1,2,4-triazol-4-ylurea, FIG. 7*c*), and 4-4 (indoleacetic acid, FIG. 7*d*) recorded together with K-Ras protein as target according to Example 4. Solid lines refer to sample (A) (ligand without target) and dashed lines refer to sample (B) (ligand plus target).

EXAMPLE 1: EXEMPLARY EVALUATION OF THE POLARIZABILITY OF A LIGAND WITH THE PHOTO-CHEMICALLY INDUCED DYNAMIC NUCLEAR POLARIZATION METHOD

The sample containing the ligand (e.g., tofacitinib) and the photosensitizer (e.g. fluorescein) at exemplary concentrations of 100 and 25 μM, respectively was prepared in deuterated water, and in an appropriate buffer, e.g., phosphate buffer 50 mM, pH=7.0.

The NMR spectra were recorded with a 600 MHZ NMR spectrometer, with a FID duration of 8192 points (68 ms), and the acquisition is performed with a single scan. The spectra were processed with an exponential decay apodization function with a line broadening of 10 Hz.

First, a non-irradiated spectrum (a) was recorded by applying the step (iii) as described in the present method (but without irradiation). The 1D $^1$H-NMR spectrum of the sample was recorded in the absence of irradiation, subsequently apodised, Fourier transformed and stored. Apodization and Fourier transformation are optional and the FID could be used for comparison with the following spectrum (b).

Second, an irradiated spectrum (b) was recorded by applying successively steps (ii)/(iii) as described in the present method. The sample was irradiated for 4 seconds at a power of 1 Watt and a wavelength of 532 nm. The 1D $^1$H-NMR spectrum of the irradiated sample is recorded, apodised, subsequently Fourier transformed and stored. Again, apodization and Fourier transformation are optional and the FID could be used for comparison with the spectrum (A).

FIG. 5 shows the 1D $^1$H NMR spectra of tofacitinib (100 μM) not preceded (step (iii)) and preceded by irradiation (step (ii)/(iii)) in the presence of fluorescein (25 μM).

The area under the curve of the peak with the apparent higher enhancement (as routinely determined by the skilled person on a case-by-case basis) is measured in spectrum (b) ($I_{irr}$), and in spectrum (a) the area under the curve is measured for the same frequency range as in spectrum (b) ($I_{dark}$). The ratio of $I_{irr}$ and $I_{dark}$ provides the signal-to-noise enhancement:

$$\rho = \frac{I_{irr}}{I_{dark}} = \frac{932489}{15357} = 60.7$$

A minimal value of 5 for the integral ratio at 600 MHz is required to consider the ligand as efficiently polarized. If measured at 200 MHz a minimal value of 25 is required, in between the values scale linearly.

Now that the tofacitinib is identified as a photo-CIDNP active ligand, further photosensitizers can be tested by repeating the irradiation/NMR spectra recording (spectrum (c), steps (ii)/(iii)) to determine, by comparing the signal's area under the curve of spectrum (c) with the signal's area under the curve of the spectrum (a), whether or not the photosensitizer is suitable for photo-CIDNP.

EXAMPLE 2A: EXEMPLARY EVALUATION OF THE BINDING OF DIFFERENT PEPTIDE LIGANDS COMPRISING AN N-TERMINAL TRYPTOPHAN RESIDUE TO THE PDZ PROTEIN DOMAIN

Several peptides containing an N-terminus (N-ter) tryptophan residue were evaluated for activity against the PDZ protein domain, the peptides were acquired from GLS-china at a purity of 99% and the PDZ domain was expressed recombinantly. The tryptophan signals in the N-ter were polarizable in the presence of fluorescein with a 50-fold signal-to-noise enhancement. The samples were prepared as follows: 100 μM peptide, 25 μM fluorescein, degassed with an enzymatic cocktail glucose oxidase (10 nM) catalase (20 nM) and glucose (1.5 mM), with PDZ 100 μM (sample B) or without (sample A). The sample was irradiated at 450 nm wavelength, 1-Watt power for 4 seconds. The samples were measured with the pulse sequences described in FIG. 2*a*) without spin lock. The spectrum of the sample A and B were recorded with a 180° phase (opposite), respectively. The results are displayed in FIG. 2*b*). Peptide 1 (WVSAV, SEQ ID NO: 1) was binding to the target PDZ and the signal was strongly modified in the presence of the target. For the peptides that did not bind such as 2 (WENEQVSAV-$NH_2$, SEQ ID NO: 2), 3 (WEQLT, SEQ ID NO: 3), and 4 (WVSAV-$NH_2$, SEQ ID NO: 4), the signal was not perturbed by the presence of the target. Therefore, when the spectra with and without target were added together, the spectra cancel each other if there is no interaction between the ligand and the target, as the phases of the two spectra are opposite. In the case of peptide 1, the difference between the signal is important. This difference could be plotted as in FIG. 2*c*) to visualize the 'hits' molecules. In this case, the differences were calculated and plotted manually. However, this could be readily automatized using a signal integration program (e.g. Topspin, Mestrenova, python package nmrglue, etc.). In this example, the difference between interacting and non-interacting molecule data is demonstrated. The same process can be applied on a bigger scale, e.g., to a library of ligands in a high-throughput assay.

Table 1 shows the signal-to-noise enhancements (SNE) of an exemplary selection of ligands after photo-CIDNP polarization. The SNE was obtained as described in example 1. The samples containing the ligands at exemplary concentrations of 100 μM and the photosensitizers fluorescein, AT12 and FMN at exemplary concentrations of 25 μM, and thionine and methylene blue at exemplary concentrations of 75 μM. The samples were prepared with 5% deuterated water and in an appropriate buffer, e.g., phosphate buffer 50 mM, pH=7.0. Prior to recording the NMR spectra, the samples were irradiated during 2 seconds with light at a different wave length depending on the photosensitizers: 450 nm (fluorescein, FMN), 532 nm (AT12), and 638 nm (thionine, methylene blue). The NMR spectra were recorded with a 600 MHz NMR spectrometer, with an FID duration of 8192 points (68 ms), and the acquisition is performed with a single scan. The spectra were processed with an exponential decay apodization function with a line broadening of 10 Hz.

The photosensitizers' IUPAC denomination are provided as follows: fluorescein: 3',6'-dihydroxyspiro[2-benzofuran-3,9'-xanthene]-1-one; AT12: [9-[2-[3-carboxypropyl (methyl)-carbamoyl]phenyl]-6-(dimethylamino)thioxanthen-3-ylidene]-dimethylazanium; thionine: (7-aminophenothiazin-3-ylidene) azanium; methylene blue: [7-(dimethylamino) phenothiazin-3-ylidene]-dimethylazanium; FMN: (2R,3S,4S)-5-(7,8-Dimethyl-2,4-dioxo-3,4-dihydrobenzo[g]pteridin-10 (2H)-yl)-2,3,4-trihydroxypentyl dihydrogen phosphate.

TABLE 1

Examples of ligands polarized with photo-CIDNP and corresponding signal-to-noise enhancement (SNE)

| Photosensitizer | Molecule | SNE |
|---|---|---|
| Fluorescein | 4-amino-N-(4-methylpyrimidin-2-yl)benzene-1-sulfonamide | 8 |
| Fluorescein | 2-{[3-(trifluoromethyl)phenyl]amino}pyridine-3-carboxylic acid | 42 |
| Fluorescein | 6-[4-(1-cyclohexyl-1H-1,2,3,4-tetrazol-5-yl)butoxy]-1,2,3,4-tetrahydroquinolin-2-one | 15 |
| Fluorescein | 1-hydrazinylphthalazine | 21 |
| Fluorescein | 6-chloro-7-{[2-(morpholin-4-yl)ethyl]amino}-5,8-dihydroquinoline-5,8-dione | 7 |
| Fluorescein | (1r,4r)-4-[2-(butylamino)-5-{4-[(4-methylpiperazin-1-yl)methyl]phenyl}-7H-pyrrolo[2,3-d]pyrimidin-7-yl]cyclohexan-1-ol | 22 |
| Fluorescein | 3-cyclopropyl-1-(3-{6-[(morpholin-4-yl)methyl]-1H-1,3-benzodiazol-2-yl}-1H-pyrazol-4-yl)urea | 15 |
| Fluorescein | 5-chloro-N-(4,5-dihydro-1H-imidazol-2-yl)-2,1,3-benzothiadiazol-4-amine | 7 |
| Fluorescein | 1-{2-[(2,4-dimethylphenyl)sulfanyl]phenyl}piperazine | 8 |
| Fluorescein | 3-amino-N-[3-(4-amino-4-methylpiperidin-1-yl)pyridin-2-yl]-6-[3-(trifluoromethyl)pyridin-2-yl]pyrazine-2-carboxamide | 12 |
| Fluorescein | 2-{3-[3-(5-hydroxypyridin-2-yl)-1,2,4-oxadiazol-5-yl]-2,2-dimethylpropanamido}cyclohex-1-ene-1-carboxylic acid | 15 |
| Fluorescein | 4-hydroxy-8-oxa-11-azatricyclo[7.5.0.0$^{2}$,$^{7}$]tetradeca-1(9),2,4,6-tetraen-10-one | 22 |
| Fluorescein | N-(1H-indazol-5-yl)acetamide | 18 |
| Fluorescein | 4-hydroxy-8,14-dithia-11-azatricyclo[7.5.0.0$^{2}$,$^{7}$]tetradeca-1(9),2,4,6-tetraen-10-one | 10 |
| Fluorescein | 3-chloro-2-methyl-N-{4-[2-(4-methylpiperazin-1-yl)-2-oxoethyl]-1,3-thiazol-2-yl}benzene-1-sulfonamide | 14 |
| Fluorescein | 1-ethyl-6-fluoro-4-oxo-7-(piperazin-1-yl)-1,4-dihydroquinoline-3-carboxylic acid | 10 |
| Fluorescein | 3-[3-{{[(2R,3S,4R,5R)-5-{4-amino-7H-pyrrolo[2,3-d]pyrimidin-7-yl}-3,4-dihydroxyoxolan-2-yl]methyl}(propan-2-yl)amino)propyl]-1-(4-tert-butylphenyl)urea | 45 |
| Fluorescein | 3-methyl-1-phenyl-4,5-dihydro-1H-pyrazol-5-one | 22 |
| Fluorescein | 2-(1,3-thiazol-4-yl)-1H-1,3-benzodiazole | 20 |
| Fluorescein | 5-fluoro-2-{[-1-amino}-6-[(5-methyl-1H-pyrazol-3-yl)amino]pyridine-3-carbonitrile | 10 |
| Fluorescein | 2-(pyridin-4-yl)-1H,4H,5H,6H,7H-pyrrolo[3,2-c]pyridin-4-one | 11 |
| Fluorescein | 4-[(1E)-2-phenylethenyl]pyrimidin-2-amine | 12 |
| Fluorescein | (R)-imino(methyl)(1-{6-[(3R)-3-methylmorpholin-4-yl]-2-{1H-pyrrolo[2,3-b]pyridin-4-yl}pyrimidin-4-yl}cyclopropyl)-$\lambda^{6}$-sulfanone | 19 |
| Fluorescein | (8R)-3-[(2R,4S,5R)-4-hydroxy-5-(hydroxymethyl)oxolan-2-yl]-3H,4H,7H,8H-imidazo[4,5-d][1,3]diazepin-8-ol | 104 |
| Fluorescein | 7-cyclopentyl-N,N-dimethyl-2-{[5-(piperazin-1-yl)pyridin-2-yl]amino}-7H-pyrrolo[2,3-d]pyrimidine-6-carboxamide | 9 |
| Fluorescein | 3-[(3R,4R)-4-methyl-3-[methyl({7H-pyrrolo[2,3-d]pyrimidin-4-yl})amino]piperidin-1-yl]-3-oxopropanenitrile | 68 |
| Fluorescein | 4,6-dimethylpyridin-2-amine | 7 |
| Fluorescein | 4H-furo[3,2-b]pyrrole-5-carboxylic acid | 44 |
| Fluorescein | 4-(5-methylthiophen-2-yl)-1,3-thiazol-2-amine | 19 |
| Fluorescein | (7Z)-N-(3,4-dimethylphenyl)-5-methyl-4H,7H-[1,2,4]triazolo[1,5-a]pyrimidin-7-imine | 7 |
| Fluorescein | (3S)-3-amino-1-hydroxy-1,2,3,4-tetrahydroquinolin-2-one | 7 |
| Fluorescein | 4H-thieno[3,2-b]pyrrole-5-carboxylic acid | 103 |
| Fluorescein | 1-phenylpyrazolidin-3-one | 33 |
| Fluorescein | Methyl 4-(4-fluorophenyl)-1-piperazinecarboxylate | 40 |
| Fluorescein | N-[(4-Methyl-2-morpholinyl)methyl]-1,3-thiazol-2-amine | 100 |
| Fluorescein | 4-(4-ethylphenyl)-5-methyl-1,3-thiazol-2-amine | 25 |
| Fluorescein | N-(propan-2-yl)-1H-1,3-benzodiazol-2-amine | 31 |
| Fluorescein | 5-(piperidin-1-yl)-1,2,3,4-tetrahydropyrimidine-2,4-dione | 29 |
| Fluorescein | ethyl[(1H-indol-4-yl)methyl]amine | 25 |
| AT12 | N-(2-phenylethyl)-1H-benzimidazol-2-amine | 6 |
| AT12 | 2-[(1H-benzimidazol-2-ylamino)methyl]phenol | 8 |
| AT12 | 3-[2-(dimethylamino)ethyl]-1H-indol-4-ol | 61 |
| AT12 | [2-(1H-indol-3-yl)ethyl]dimethylamine | 14 |
| AT12 | 2-(2,5-Dimethoxy-4-ethylthiophenyl)-N-[(2-methoxyphenyl)methyl]ethanamine | 8 |
| AT12 | 2-[2,5-Dimethoxy-4-(ethylthio)phenyl]ethanamine•hydrochloride | 7 |
| AT12 | N-(3-Trifluoromethylphenyl)-piperazine | 10 |
| AT12 | 7-methoxy-1-methyl-3H,4H,9H-pyrido[3,4-b]indole | 42 |
| AT12 | N-[2-(5-methoxy-1H-indol-3-yl)ethyl]acetamide | 45 |
| AT12 | 5-methyl-2-(3-methylphenyl)-imidazole-4-carboxylic acid | 9 |
| AT12 | 2-[20-carbamoyl-12-[4-(diaminomethylideneamino)butyl]-3-(1H-indol-3-ylmethyl)-2,5,8,11,14,22-hexaoxo-17,18-dithia-1,4,7,10,13,21-hexazabicyclo[21.3.0]hexacosan-6-yl]acetic acid | 56 |
| FMN | N-(3-Trifluoromethylphenyl)-piperazine | 90 |
| FMN | 1-(1,3-Benzodioxol-5-yl)propan-2-amine | 29 |
| FMN | [2-(1H-indol-3-yl)ethyl]dimethylamine | 11 |

TABLE 1-continued

| Examples of ligands polarized with photo-CIDNP and corresponding signal-to-noise enhancement (SNE) | | |
|---|---|---|
| Photosensitizer | Molecule | SNE |
| FMN | 3-[2-(dimethylamino)ethyl]-1H-indol-4-ol | 17 |
| Thionine | 2-(1H-indol-3-yl)ethan-1-amine | 15 |
| Thionine | 4-(2-aminoethyl)phenol | 17 |
| Thionine | N,N-dimethyl-1,2,3,4-tetrahydroquinoline-6-carboxamide | 10 |
| Thionine | 2-{[(1H-1,3-benzodiazol-2-yl) amino]methyl}phenol | 8 |
| Thionine | N-(4-hydroxyphenyl)-2-methoxyacetamide | 9 |
| Thionine | 1-(2-ethoxyphenyl)piperazine | 10 |
| Thionine | N-(2-phenylethyl)-1H-1,3-benzodiazol-2-amine | 8 |
| Thionine | 2,3-dihydro-1H-indole-5-carboxamide | 9 |
| Thionine | N-(propan-2-yl)-1H-1,3-benzodiazol-2-amine | 7 |
| Thionine | 2-(thiophen-2-yl)-1H-imidazole | 9 |
| Methylene Blue | 4-(2-aminoethyl)phenol | 16 |

EXAMPLE 2B: DETERMINATION OF THE DISSOCIATION CONSTANT OF THE PEPTIDE LIGAND BINDING TO THE PDZ Protein Domain Peptide 1 (WVSAV, SEQ ID NO: 1) was titrated in the presence of the PDZ protein domain. The samples were prepared as follows: 47 μM peptide, 25 μM fluorescein, degassed with an enzymatic cocktail glucose oxidase (100 nM) catalase (120 nM) and glucose (1.5 mM), with a series of PDZ protein domain concentrations (4, 10, 17, 29, 41, 49, 57, 72, 79 for sample B-I to B-IX, respectively) or without (sample A). The sample was irradiated at 450 nm wavelength, 1-Watt power with a series of irradiation time (0, 25, 50, 100, 200, 300, 400, 450, 500, 600, 700, 800, 900, 1000, 1500, and 2000 milliseconds). The sample A was repeated twice to verify repeatability. The samples were measured for each irradiation time with the pulse sequences described in FIG. 2*a*) without spin lock. The polarization rate (kP) was obtained from sample A initial rate (FIG. 2*d-a*). The polarization signal integrals ratio as described in equation (7), $L^*_B/L^*_A$, was calculated by dividing the signal integral at 7.4 ppm (FIG. 2*b*) in the presence of PDZ protein domain target by the signal at 7.4 ppm (FIG. 2*b*) in the absence of PDZ protein domain target. The polarization ration was calculated for each PDZ protein domain concentration, respectively. The equation (7) was fitted to obtain the free ligand concentration $L_{free}$. The free ligand concentrations ($L_{free}$) were used to obtain $L_{bound}/L$ at different PDZ protein domain concentrations (FIG. 2*d-b*) were used to fit equation (6) and a dissociation constant (Kd) of 7 μM is obtained.

EXAMPLE 3: EVALUATION OF THE BINDING OF DIFFERENT SMALL ORGANIC MOLECULES LIGANDS TO THE PIN1 PROTEIN

Several ligands with different molecular scaffolds were evaluated for activity against the PIN1 protein (peptidyl-prolyl cis-trans isomerase NIMA-interacting 1), the ligand 3-1 (5-methyl-2-(3-methylphenyl)-imidazole-4-carboxylic acid), ligand 3-2 (5-methyl-indole-3-carboxylic acid), ligand 3-3 (tryptophan) and ligand 3-4 (4-hydroxy-8-oxa-11-aza-tricyclo[7.5.0.0$^{2,7}$]tetradeca-1 (9),2,4,6-tetraen-10-one) were acquired from Enamine, Specs, and Sigma Aldrich, and MedChem Express Europe, respectively, and the PIN1 protein was expressed recombinantly according to standard protocols. The polarizabilities of the small molecules were verified according to Example 1, and provided a signal enhancement of 31-fold for ligand 3-1,6-fold for ligand 3-2, and 50-fold for ligand 3-3. The samples were prepared as follows: 100 μM ligand, 25 μM fluorescein, degassed with an enzymatic cocktail glucose oxidase (10 nM) catalase (20 nM) and glucose (1.5 mM), and sample (B) comprise 50 μM PIN1 protein. The sample comprising ligand 3-4 was prepared as follows: 25 μM ligand, 15 μM fluorescein, degassed with an enzymatic cocktail glucose oxidase (10 nM) catalase (20 nM) and glucose (1.5 mM), and sample (B) comprised 25 μM PIN1 protein.

The samples (A) and (B) were irradiated at 450 nm wavelength, 1-Watt power for 2 seconds. The samples were measured with the pulse sequences described in FIG. 2*a*) without spin lock. The results are displayed in FIG. 6. The ligand 3-1, 3-2 and 3-4 bound to the target PIN1 and the signal was modified in the presence of the target, this was observed by visually comparing the dashed (sample (B)) and solid (sample (A)) spectra in FIGS. 6*a, b* and *d* for ligand 3-1, 3-2 and 3-4, respectively. For the ligand 3-3, which did not bind, the signal was not perturbed by the presence of the target (FIG. 6*c*), this was observed as the dashed and solid spectra overlap perfectly. The ligands 3-1 and 3-2 are known inhibitors of the PIN1 protein (Potter et al., 2010, Bioorg Med Chem Lett, Vol 20, p. 6483-6488), and tryptophan has been verified to not bind to PIN1. The ligand 3-4 was a newly discovered inhibitor, it shows strong structural similarity with the ligands 3-1 and 3-2 and it demonstrates the capacity of detecting ligands at low concentrations (25 μM).

EXAMPLE 4: EVALUATION OF THE BINDING OF DIFFERENT SMALL ORGANIC MOLECULES LIGANDS TO THE K-RAS PROTEIN

Several ligands with different molecular scaffolds are evaluated for activity against the K-Ras protein. The ligand 4-1 (5 N-(Furan-2-ylmethyl)-1H-benzimidazol-2-amine)-imidazole-4-carboxylic acid), ligand 4-2 (N-[2-(5-fluoro-1H-indol-3-yl)ethyl]acetamide), ligand 4-3 (N-(2-methoxy-5-methylphenyl)-N'-4H-1,2,4-triazol-4-ylurea), and 4-4 (indoleacetic acid) were acquired from Enamine, and the K-Ras protein was expressed recombinantly according to standard protocols. The polarizabilities of the small molecules were verified according to Example 1, and yielded signal enhancement of 13-fold for ligand 4-1, 19-fold for ligand 4-2, and 30-fold for ligand 4-3, 19-fold for the ligand 4-4. The samples were prepared as follows: 500 μM ligand, 25 μM fluorescein, degassed with an enzymatic cocktail glucose oxidase (10 nM) catalase (20 nM) and glucose (1.5 mM), and sample (B) comprising 100 μM K-Ras protein.

The samples (A) and (B) were irradiated at 450 nm wavelength, 1-Watt power for 2 seconds, and the NMR spectra were recorded according to the pulse sequence described in FIG. 2*a*. A spinlock was applied after the detection pulse with an orthogonal phase for 200 ms at a power of 10 KHz. The spinlock acts as a $T_{1,rho}$ filter which facilitates the identification of very weak binders (up to 20 mM). The results are displayed in FIG. 7. The ligand 4-1, 4-2, and 4-3 bound to the target K-Ras and the signal was modified in the presence of the target, this was observed by visually comparing the dashed (sample (B)) and solid (sample (A)) spectra in the FIGS. 7*a, b*, and *c* for ligand 4-1, 4-2, and 4-3 respectively. For the ligand 4-4, which did not bind, the signal was not perturbed by the presence of the target (FIG. 7*d*), this was observed as the dashed and solid spectra overlapped. The ligands 4-1, 4-2, 4-3 have been identified to bind K-Ras from state-of-the-art NMR techniques (STD), and cross-validated using HSQC. Ligand 4-4 has been verified to not bind with K-Ras.

```
                              SEQUENCE LISTING


Sequence total quantity: 4
SEQ ID NO: 1            moltype = AA  length = 5
FEATURE                 Location/Qualifiers
REGION                  1..5
                        note = Peptide 1
source                  1..5
                        mol_type = protein
                        organism = synthetic construct
SEQUENCE: 1
WVSAV                                                                     5

SEQ ID NO: 2            moltype = AA  length = 9
FEATURE                 Location/Qualifiers
REGION                  1..9
                        note = Peptide 2
MOD_RES                 9
                        note = AMIDATION
source                  1..9
                        mol_type = protein
                        organism = synthetic construct
SEQUENCE: 2
WENEQVSAV                                                                 9

SEQ ID NO: 3            moltype = AA  length = 5
FEATURE                 Location/Qualifiers
REGION                  1..5
                        note = Peptide 3
source                  1..5
                        mol_type = protein
                        organism = synthetic construct
SEQUENCE: 3
WEQLT                                                                     5

SEQ ID NO: 4            moltype = AA  length = 5
FEATURE                 Location/Qualifiers
REGION                  1..5
                        note = Peptide 4
MOD_RES                 5
                        note = AMIDATION
source                  1..5
                        mol_type = protein
                        organism = synthetic construct
SEQUENCE: 4
WVSAV                                                                     5
```

The invention claimed is:

1. A method for detecting, and/er characterizing, or detecting and characterizing a ligand-target binding based on photochemically induced dynamic nuclear polarization (photo-CIDNP) enhanced NMR spectroscopy, the method comprising the following steps:

(i) providing a sample (A) comprising a photosensitizer and a ligand, wherein the photosensitizer is suitable for chemically inducing dynamic nuclear polarization of the ligand upon irradiation of the sample;

(ii) irradiating sample (A) at a wavelength and duration suitable for exciting the photosensitizer and under conditions allowing for chemically induced dynamic nuclear polarization of the ligand by the photosensitizer;

(iii) recording an NMR spectrum of sample (A);

(iv) providing a sample (B) comprising sample (A) and further comprising a target of interest;

(v) irradiating sample (B) under the conditions of step (ii);

(vi) recording an NMR spectrum of sample (B); and (vii) comparing the NMR spectra of steps (iii) and (vi) and detecting, characterizing, or detecting and characterizing a ligand-target binding based on at least one difference in the NMR spectra of steps (iii) and (vi).

2. The method according to claim 1, wherein after positively detecting the binding of the ligand to the target in sample (B), the method further comprises the steps:

(viii) providing a sample (C) comprising sample (B) and a further ligand;

(ix) irradiating sample (C) under the conditions of step (ii), wherein:

the further ligand is essentially not suitable for chemically induced dynamic nuclear polarization, the photosensitizer is essentially not suitable for chemically inducing dynamic nuclear polarization of the further ligand, or both;

(x) recording an NMR spectrum of sample (C); and (xi) comparing the NMR spectra of steps (vi) and (x) and detecting, characterizing, or detecting and characterizing a competitive binding of the further ligand to the target based on at least one difference in the NMR spectra of steps (vi) and (x).

3. The method according to claim 2, wherein after positively detecting the competitive binding of the further ligand to the target in sample (C), the method further comprises the steps:

(xii) providing a sample (D) comprising sample (A) and the further ligand of sample (C);

(xiii) irradiating sample (D) under the conditions of step (ii), wherein:

the further ligand is essentially not suitable for chemically induced dynamic nuclear polarization, the photosensitizer is essentially not suitable for chemically inducing dynamic nuclear polarization of the further ligand, or both:

(xiv) recording an NMR spectrum of sample (D); and (xv) comparing the NMR spectra of steps (iii) and (xiv) and validating the detection and/or characterization of the competitive binding of the further ligand to the target based on an absence of a difference in the NMR spectra of steps (iii) and (xiv).

4. The method according to claim 3, wherein the NMR spectrum in step (xiv) is a Fourier-transformed NMR spectrum and the at least one difference in the NMR spectra in step (xv) is selected from a difference in the area under the curve of a signal, a difference in the intensity of a signal, a difference in the shape of the curve of a signal, a difference in the width of the curve of a signal, a difference in the chemical shift of the signal, and the absence, presence and/or nature of spin couplings.

5. The method according to claim 4, wherein the difference in the intensity of a signal, the difference in the area under the curve of a signal, or both, is at least $\sqrt{2}$-fold the noise.

6. The method according to claim 2, wherein at least one of:

(a) the further ligand is an organic ligand;

(b) the molecular mass of the further ligand is lower than the molecular mass of the target;

(c) the molar ratio between the further ligand and the target is about 1:1 or greater than 1:1 (further ligand to target); and (d) a combination thereof.

7. The method according to claim 2, wherein the further ligand is in solution.

8. The method according to claim 2, wherein the further ligand is a nucleic acid, an amino acid, a (poly-)peptide, a mono- or polysaccharide, an antibody, an antibody fragment, a peptidoglycan, a proteoglycan, a terpene, or a small organic molecule.

9. The method according to claim 2, wherein the NMR spectrum in step (x) is a Fourier-transformed NMR spectrum and the at least one difference in the NMR spectra in step (xi) is selected from a difference in the area under the curve of a signal, a difference in the intensity of a signal, a difference in the shape of the curve of a signal, a difference in the width of the curve of a signal, a difference in the chemical shift of the signal, and the absence, presence and/or nature of spin couplings.

10. The method according to claim 9, wherein the difference in the intensity of a signal, the difference in the area under the curve of a signal, or both, is at least $\sqrt{2}$-fold the noise.

11. The method according to claim 2, wherein an association or dissociation constant of the further ligand to the target is calculated based on a decay or accumulation in the nuclear polarization of the further ligand in sample (B) and (C).

12. The method according to claim 1, wherein at least one of:

(a) the ligand is an organic ligand;

(b) the target is an inorganic or organic target;

(c) the molecular mass of the ligand is lower than the molecular mass of the target;

(d) the molar ratio between the ligand and the target is about 1:1 or greater than 1:1 (ligand to target); and (e) a combination thereof.

13. The method according to claim 1, wherein at least one of:

the ligand is in solution, the target is a solid, an immobilized target or a target in solution, and a combination thereof.

14. The method according to claim 1, wherein the ligand comprises a chemical entity selected from the group consisting of (a) monocyclic aromatic $C_5$-$C_7$ moieties and/or a-bicyclic aromatic $C_7$-$C_{12}$ moieties substituted by one or more heteroatoms;

(b) heteromonocyclic aromatic $C_1$-$C_6$ moieties comprising 1 to 5 heteroatoms or heterobicyclic aromatic $C_2$-$C_{11}$ moieties comprising 1 to 8 heteroatoms; and (c) a secondary or tertiary amine, a sulfoxide, a dialkylsufide, a sulfamide, or a sulfamate.

15. The method according to claim 1, wherein the ligand is a nucleic acid, an amino acid, a (poly-)peptide, a mono- or polysaccharide, an antibody, an antibody fragment, a peptidoglycan, a proteoglycan, a terpene, or a small organic molecule.

16. The method according to claim 1, wherein the photosensitizer is selected from the group consisting of flavine, bipyridyl, benzophenone, xanthene, thionine, rhodamine, thiopyronine, benzothiopyronine, oxazine, phenoxazine, acridine, anthraquinone, coumarine, and arylmethine.

17. The method according to claim 1, wherein the target is selected from the group consisting of a (poly-)peptide, an oligo/polynucleotide, an oligo/polysaccharide, a macromolecular assembly, an organic polymer, and a microporous material.

18. The method according to claim 1, wherein the NMR spectrum is selected from the group consisting of a $^{1}H$, $^{13}C$, $^{15}N$, $^{19}F$ and $^{31}P$ spectrum.

19. The method according to claim 1, wherein the NMR spectra in steps (iii) and (vi) are Fourier-transformed NMR spectra and the at least one difference in the NMR spectra in step (vii) is selected from a difference in the area under the curve of a signal, a difference in the intensity of a signal, a difference in the shape of the curve of a signal, a difference in the width of the curve of a signal, a difference in the chemical shift of the signal, and the absence, presence or nature of spin couplings.

20. The method according to claim 19, wherein the difference in the intensity of a signal, the difference in the area under the curve of a signal, or both, is at least $\sqrt{2}$-fold the noise.

21. The method according to claim 1, wherein an association or dissociation constant of the ligand to the target is calculated based on a decay or accumulation in the nuclear polarization of the ligand in sample (A) and (B).

22. A method for determining the structure of a ligand-target complex, the method comprising the following steps:

(II) providing a sample comprising a ligand bound to a target and a photosensitizer, wherein the photosensitizer is suitable for chemically inducing dynamic nuclear polarization of the ligand upon irradiation of the sample;

(III) irradiating the sample at a wavelength and duration suitable for exciting the photosensitizer and under conditions allowing for chemically induced dynamic nuclear polarization of the ligand by the photosensitizer;

(IV) recording a nuclear Overhauser effect (NOE) 2D NMR spectrum;

(V) determining the structure of the ligand-target complex based on the NOE 2D NMR spectrum.

23. A device for conducting the method according to claim 1, the device comprising:

(a) a sample holder, wherein the sample holder has a bottom and a top and comprises sample (A) and (B) according to claim 1;

(b) an NMR device comprising a sample tube and a light-emitting device, wherein the sample tube is in fluid communication with the sample holder and the light-emitting device is configured to irradiate and excite the photosensitizer allowing for chemically induced dynamic nuclear polarization of the ligand in the sample in the sample tube within the NMR device;

(c) a pump configured to move a sample from the sample holder to the sample tube; and (d) at least one processing unit configured to (d1) synchronize the movement of the sample from the sample holder to the sample tube with a measurement operation of the NMR device.

24. The device according to claim 23, wherein the sample tube is in the form of a coaxial sample tube comprising an inner tube having a top and a bottom positioned within an outer tube having a top and a closed bottom and configured to receive the sample.

25. The device according to claim 24, wherein at least one of:

the inner tube comprises an inlet tubing configured to transfer a sample from the sample holder through the inner tube to the outer tube, the inner tube comprises the light emitting device, the inner tube comprises a buffer, the inner tube has an etched inner surface, an etched outer surface, or both, and a combination thereof.

26. A method for determining the structure of a ligand-target complex, the method comprising the following steps:

(I) determining, characterizing or determining and characterizing a ligand-target binding according to claim 1;

(II) providing a sample comprising a ligand bound to a target and a photosensitizer, wherein the photosensitizer is suitable for chemically inducing dynamic nuclear polarization of the ligand upon irradiation of the sample;

(III) irradiating the sample at a wavelength and duration suitable for exciting the photosensitizer and under conditions allowing for chemically induced dynamic nuclear polarization of the ligand by the photosensitizer;

(IV) recording a nuclear Overhauser effect (NOE) 2D NMR spectrum;

(V) determining the structure of the ligand-target complex based on the NOE 2D NMR spectrum.

27. The device according to claim 23, wherein the at least one processing unit is further configured to at least one of:

(d2) compare the NMR spectra;

(d3) detect, characterize, or detect and characterize a ligand-target binding;

(d4) calculate an association constant;

(d5) determine and provide structural data of a ligand-target complex; and (d6) a combination thereof.

* * * * *